(12) United States Patent
Cong

(10) Patent No.: US 9,181,172 B2
(45) Date of Patent: Nov. 10, 2015

(54) RHEIN CONJUGATES, PREPARATION METHOD THEREOF AND THEIR USES IN PRODUCING MEDICINES FOR TREATING DIABETIC NEPHROSIS, INTESTINAL ADHESION AND OSTEOARTHRITIS

(76) Inventor: Xiaodong Cong, Jiangsu (CN)

( * ) Notice: Subject to any disclaimer, the term of this patent is extended or adjusted under 35 U.S.C. 154(b) by 1843 days.

(21) Appl. No.: 11/995,363

(22) PCT Filed: Jul. 10, 2006

(86) PCT No.: PCT/CN2006/001634
§ 371 (c)(1),
(2), (4) Date: Jan. 11, 2008

(87) PCT Pub. No.: WO2007/012254
PCT Pub. Date: Feb. 1, 2007

(65) Prior Publication Data
US 2008/0207758 A1 Aug. 28, 2008

(30) Foreign Application Priority Data

Jul. 11, 2005 (CN) .......................... 2005 1 0040963

(51) Int. Cl.
| C07C 65/34 | (2006.01) |
| A61K 31/192 | (2006.01) |
| A61P 19/02 | (2006.01) |
| A61P 3/00 | (2006.01) |
| A61P 1/00 | (2006.01) |
| C07C 66/02 | (2006.01) |
| A61K 31/197 | (2006.01) |
| A61K 31/198 | (2006.01) |
| A61K 31/4965 | (2006.01) |

(52) U.S. Cl.
CPC .............. *C07C 66/02* (2013.01); *A61K 31/192* (2013.01); *A61K 31/197* (2013.01); *A61K 31/198* (2013.01); *A61K 31/4965* (2013.01)

(58) Field of Classification Search
None
See application file for complete search history.

(56) References Cited

U.S. PATENT DOCUMENTS

| 5,652,265 A * | 7/1997 | Vittori et al. .................. 514/548 |
| 5,864,048 A | 1/1999 | DiNapoli |
| 5,986,129 A * | 11/1999 | Di Napoli ..................... 562/461 |
| 2004/0052826 A1 * | 3/2004 | Fernandez-Kleinlein et al. .............................. 424/401 |
| 2004/0198695 A1 * | 10/2004 | Li et al. ............................ 514/54 |
| 2005/0129781 A1 | 6/2005 | Skiendzielewski et al. |

FOREIGN PATENT DOCUMENTS

| CN | 1178669 A | 4/1998 |
| CN | 1547468 A | 11/2004 |
| CN | 1712041 A | 12/2005 |
| WO | WO-92-10464 | * 6/1992 |

OTHER PUBLICATIONS

Application No. PCT/CN2006/001634, International Preliminary Report on Patentability and the Written Opinion of the International Searching Authority dated Nov. 23, 2006. 5 pages.
Mohri, Fumihito, Molecular orbital study of bond-valence sum rule for hydrogen bond systems using Lewis-electron pair theory, Journal of Molecular Structure: THEOCHEM 756 (2005) 25-33, Available online Nov. 2, 2005, 9 pages.
Del Bene, Janet E., et al., What a difference a decade makes: progress in ab initio studies of the hydrogen bond, Journal of Molecular Structure: THEOCHEM 573 (2001) 11-23, Revised Jan. 31, 2001, Accepted Feb. 5, 2001, 13 pages.
Morissette, Sherry L., et al., High-throughput crystallization: polymorphs, salts, co-crystals and solvates of pharmaceutical solids, Science Direct: Advanced Drug Delivery Reviews 56 (2004) 275-300, 26 pages.
Shan, Ning, et al., The role of cocrystals in pharmaceutical science, Drug Discovery Today, vol. 13, Nos. 9/10, Published May 2008, 7 pages.
Lara-Ochoa, F., et al., Cocrystals Definitions, Supramolecular Chemistry, 19: 8, 553-557, Published Sep. 25, 2007 (iFirst), 6 pages.
Yui, Nobuhiko, PhD, et al., Design of polyrotaxanes as supramolecular conjugates for cells and tissues, The Japanese Society for Artificial Organs, 7:62-68, 7 pages.

* cited by examiner

*Primary Examiner* — Frederick Krass
*Assistant Examiner* — Celeste A Roney
(74) *Attorney, Agent, or Firm* — Schmeiser, Olsen & Watts, LLP

(57) ABSTRACT

The conjugates of present invention are formed by the combination of rhein or their analogues with the organic bases or amino acids in molecular force between them. The methods for preparing the conjugates and their uses for manufacturing medicines in the treatment of diabetic nephrosis, recovery of gastrointestinal function and prevention of intestinal adhesion, as well as treatment of osteoarthritis, rheumatic arthritis and rheumatoid arthritis are also described. Rhein or their analogues as the left part of general formula (I) is selected from (1) the compounds of rhein or their analogues, in which one or two substituents of R2~R3 and R6~R7 are COOH at least two substituents of R1~8 are —H; or (2) the rhein-containing extract derived from plants. In general formula (I), M represents nitrogen-containing organic bases or basic amino acids.

4 Claims, 4 Drawing Sheets

```
analytic functional testing
VarioEL III CHNS
serial number 11045069                                              13.01.06

No. Name      Weight  O2 Prot. C/N           Content Peak  Blank
              [mg]       [%]   Ratio            [%]  Area  Value
--------------------------------------------------------------------

37 DHSJAS     2.0240   1 0.000 4.590    N:   12.04  8174     0
                                        C:   55.28 26047     0
                                        S:    0.000   57    57
                                        H:    4.873 6474     0

38 DHSJAS     2.2300   1 0.000 4.581    N:   12.05  9010     0
                                        C:   55.20 28641     0
                                        S:    0.000   43    43
                                        H:    4.885 7234     0
```

FIG. 1

RHEIN CONJUGATES, PREPARATION METHOD THEREOF AND THEIR USES IN PRODUCING MEDICINES FOR TREATING DIABETIC NEPHROSIS, INTESTINAL ADHESION AND OSTEOARTHRITIS

FIELD OF THE INVENTION

The present invention relates to a medicinal conjugate, particularly relates to a conjugate formed by rhein or rhein analogues and different basic groups, preparation method thereof and their use in producing medicines for treating diabetic nephrosis, recovery of gastrointestinal function and preventing intestinal adhesion, and treating osteoarthritis, rheumatic arthritis and rheumatoid arthritis.

BACKGROUND OF THE INVENTION

In prior arts, rhein or rhein analogues has been used in the preparation of various drugs, for instance, a rhein salt disclosed in Chinese patent 200410049948, which is shown in the following two general formulae respectively:

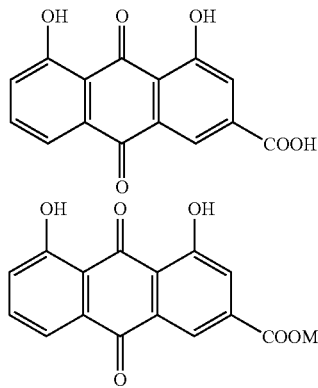

Where, M is alkali metal, alkaline-earth metal or organic alkali residues.

Rhein analogues are defined as matters extracted, refined or chemically modified form the rhein or rhein analogues such as rhubarb (Rheum palmatum L., Rheum tanguticum Maxim. Ex Balf. Or Rheum officinale Baill., Polygonum cuspidatum (Polygonum cuspidatum sieb. Et Zucc.), Folium sennae (Folium sennae), etc. The characteristic composition is rhein or rhein analogues -containing effective part, shown as the compounds with general formula (I).

According to patent search data from Chinese Pharmaceutical Abstracts (searching word "Rhein"), CNKI database (searching word "Rhein"), China patent (searching word "Rhein"), CA (Search "Accession No. 478-43-3"), US Patent (searching word "Rhein") and European Patent (searching word "Rhein"), the salts of rhein analogues include rhein sodium salt, rhein potassium salt (U.S. Pat. No. 6,197,818, CN97107137), and diacerhein [13739-02-1] (CN97192531, CN93101181, CA96: 193416) and diacerhein potassium salt (EP243968).

Diabetes is a systemic metabolic disease, despite many factors involved in the pathogenesis, insulin resistance (IR) and pancreatic β cell dysfunction are considered to be the two main components. Obesity, hypertension, hyperlipidemia, hyperuricemia and hypercoagulable state constitute IR clinical syndromes. IR often exists prior to the existence of reduction of sugar tolerance, which is not only the direct reason for the occurrence of diabetes, but also the basis of cardiovascular complications of diabetes. Diabetic nephrosis (DN) is a common complication of diabetes. Rhein has multiple functions in the aspects of sugar reduction, lipid adjustment, and improvement of insulin resistance and reduction of the urine protein excretion and so on; therefore, it can play a multi-target, multi-layered role in different phases of diabetic nephrosis, so as to achieve the purpose of prevention and treatment of diabetic nephrosis.

Abdominal surgery is the most common surgical operation. Generally the patients after operation have relatively weak gastrointestinal function; therefore, the recovery of gastrointestinal function after surgery has great significance on the patient's rehabilitation, including the recovery of diseases and reduction of complications such as intestinal adhesion, etc.

Postoperative intestinal adhesion is still an unresolved clinical surgical problem. The research reports in recent years show that 90%~100% of patients of abdominal surgery will produce postoperative intestinal adhesion [Luijendijk R W, etal Foreign material in postoperative Adhesions AnnSurg, 1996,223(3):242; Scott Coombers D.etal Human intraperitoneal fibrinolytic respond to elective surgery BrJSurg, 1995, 82:414]. Among the patients of adhesions, more than 80% of patients will form adhesions between wounds and omentum, and 50% of cases involve in small intestine [Menxies D, etal Intestinal obstruction from adhesions: How big is the problem? AnnR Coll Surg Engl, 1990, 72 (1): 60]. And the occurrence of intestinal adhesion is related to post-operative peritoneal exudation and weak enterokinesia. Reduction of exudation or improvement of enterokinesia will reduce the occurrence of adhesions. Currently the gastrointestinal dynamic drugs have strong action on the stomach and intestines, especially on the stomach, which will easily cause abdominal discomfort and vomiting. Although the medicines promoting enterokinesia can accelerate the enterokinesia, it cannot reduce the inflammatory reaction and the exudation of inflammatory substances and fibrins.

Neostigmine Bromide can cause the obvious anastalsis in the clinical application, and patients have obvious pain feeling, which cannot actually allow the recovery of gastrointestinal function [Liqishen, et al. The clinical observation of the use of rhubarb on the intestinal function recovery of postoperative patients of diffuse peritonitis, Chinese Journal of Coal Industry Medicine, 1998, 1 (4): 372)]. Clinically raw rhubarb liquid is administered [Ge Hengwen et al, clinical effect observation of recovery of postoperative gastrointestinal function of raw rhubarb liquid, Journal of Hubei Medical Staff College, 2002,15 (2), 19], or rhubarb and other traditional Chinese drug are decocted and orally administered [Huang Honghan, Clinical application study of intestinal adhesion soup, Traditional Chinese Medicine Journal 2006,5 (2), 42]. However, the clinical dose is difficult to control, and administration is inconvenient, so it is subject to restriction for clinical use.

Osteoarthritis, rheumatic arthritis and rheumatoid arthritis are higher incidence of arthrosis. Taking the former as an example, the incidence rate is about 10 percent of the total population, and for patients over 60 years old, over 50 percent of patients are affected, and for women under 45 years old, 45-60 years old and over 65 years old, the incidence rate is 2%, 30% and 68% respectively; for men, the rate is 3%, 24.5% and 58% respectively. With the ageing of the population, the morbidity is becoming more and more in the total population. At present, the main drugs for treatment of osteoarthritis mainly include steroid and non-steroid anti-inflammatory drugs. The adverse reaction of steroid anti-inflammatory drugs is generally known for the public. For the non-steroid anti-inflammatory drugs, cyclooxygenase inhibitor (COX) also has many adverse reactions, for instance, oral administration and injection will cause alimentary tract hemorrhage, and especially old people may produce adverse reactions, which is unfavorable for the diseases of high incidence for old people such as osteoarthritis.

Because rhein analogues are indissoluble in the water and cannot be completely absorbed by the gastrointestinal tract, the bioavailability becomes low which makes restriction on the application of the rhein. The salt formation by combination of rhein analogues and metal ion increases the water solubility of rhein compounds, improves the bioavailability of oral administration; because the rhein sodium salt, rhein potassium salt (U.S. Pat. No. 6,197,818, CN97107137), and diacerhein [13739-02-1] (CN97192531, CN93101181, CA96: 193416) and diacerhein potassium salt (EP243968) are strong base- weak acid salt, the solution presenting basicity, if made into hydro-acupuncture, the pH value is higher, which is unacceptable for human physiology; while if decreasing the pH value, the stability of the preparation is bad.

SUMMARY OF THE INVENTION

An object of the present invention is to provide a new compound formed by rhein analogues and different basic groups, which can not only increase the water solubility, but also can overcome the shortcomings of basicity of strong base salt solution, which is unbearable for human physiology due to its high pH value if made into fluid acupuncture, and the poor stability of the of agents if lowing the pH value of solution. Another object of the present invention is to provide a process of the aforesaid medicinal compound formed by rhein analogues and different basic groups. Rhein analogues have good water solubility and can bind with the acceptable carriers to form medical composition. The third object of the present invention is to provide the use of the aforesaid compound for the preparation of drugs in the prevention and treatment of diabetic nephrosis. Oral tablet and capsule formulations prepared by this kind of compound have increased in vitro dissolution, indicating higher bioavailability, and more worth mentioned is that they can be made into water-carrier formulations. The present invention also provides the use of the aforesaid compound for the preparation of drugs in the treatment of recovery of gastrointestinal function and prevention of intestinal adhesion. Oral tablet and capsule formulations prepared by this kind of compound have increased in vitro dissolution, indicating higher bioavailability, and made into stable water-carrier formulations. In addition, the present invention also provides the use of the aforesaid compound for the preparation of drugs in the treatment osteoarthritis, rheumatic arthritis and rheumatoid arthritis. Oral tablet and capsule formulations prepared by this kind of compound have increased in vitro dissolution, indicating higher bioavailability, and made into stable water-carrier formulations.

To achieve the above three objectives for the present invention, technical scheme for this application is described respectively as follows:

A compound of rhein or rhein analogues, which characterizes in that its structure is as the formula (I):

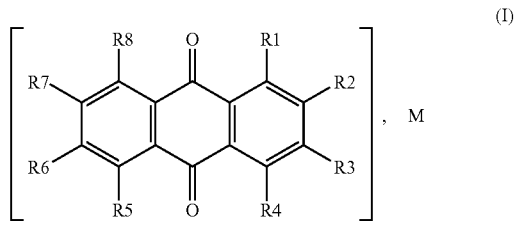

Where, the left part of the formula (I) may be either of the following:

(1) Rhein or rhein monomer composition, where 1 or 2 substituents of R2-R3, R6~47 are-COOH, and the remaining substituents of R1~R8 may be any of the following: —H, —O glucose,—OH,—OCH3,—CH3, wherein at least two —H among R1~R8;

(2)Rhein-containing extract derived from plants (referred to as "rhein-containing effective part"); where M represents nitrogen-containing organic alkali or basic amino acids. Said rhein orrhein analogues combines with nitrogen-containing organic base or basic amino acid to form compounds via intermolecalar force.

For instance, said rhein or rhein analogues combine with the nitrogen-containing organic base or basic amino acid by the hydroxyl group of -COOH to form compounds via intermolecalar force.

The aforesaid "rhein-containing effective part" refers to a group of bioactive compounds extracted, isolated and purified from plants with the same mother nucleus. In the present invention, the mother nucleus is anthraquinone.

In other words, the left part is the rhein-containing effective part of, or rhein monomer composition; where ~2 substituents of R2-R3, R6-R7 are -COOH, the remaining of R1~R8 is any of the following substituents:—H,—O-glucose,—OH,—OCH3,—CH3, wherein at lease two —H of R1~R8.

When said substituents of R1~R8 are selected, substituted from the aforesaid scope, the structural changes of this compound have no substantive impact on the nature of the medicines.

Said "the conjugates of nitrogen-containing organic base or basic amino acid and rhein or rhein analogues" is quite different from the ordinary said "rhein or rhein analogues salt".

Strong base or weak base reacts with rhein or rhein analogues to produce salts combined by ionic bond and water; however, for the conjugates of nitrogen-containing organic base or basic amino acid and rhein or rhein compound, the nitrogen-containing organic base or basic amino acid reacts with rhein or rhein analogues and do not produce water, but forms a conjugates between two molecules by intermolecalar force. No mechanism exists for the reaction process to produce water and form ionic bond. The structure can be identified by molecular weight of reagent and product before and after the reaction between rhein and arginine, the elemental analysis of rhein arginine conjugate, and the C spectrum and H spectrum and so on.

For instance, the data and results of elemental analysis of rhein arginine conjugates are shown in Table 2.

TABLE 2

| Determination of elemental analysis of rhein arginine | | | | |
|---|---|---|---|---|
| Element | C(%) | H(%) | N(%) | S(%) |
| theoretical value | 55.021 | 4.837 | 12.222 | 0.000 |
| Measured value | 55.28 | 4.873 | 12.04 | 0.000 |
|  | 55.20 | 4.885 | 12.05 | 0.000 |

As shown in Table 2, the difference of C, H, N, S elemental analysis determination value of synthesized rhein arginine and the theoretical value is less than 0.5%, which shows that the synthesized product accords with the formula C15H8O6•C6H14N4O2, and no dehydration reaction in the process.

In addition, according to the gravitational thermal analysis chart of rhein-arginine conjugate under FIG. 2, rhein-arginine conjugate contains crystal water.

Rhein arginine conjugate 13 C-NMR determination data and carbon atom attribution are shown in Table 3:

TABLE 3

| Rhein arginine conjugate 13 C-NMR determination data and carbon atom attribution | | | | | |
|---|---|---|---|---|---|
| No. of carbon atom | Chemical Shifts(δ) | No. of carbon atom | Chemical Shifts(δ) | No. of carbon atom | Chemical Shifts(δ) |
| 4' | 25.46(24.9) | 8 | 121.56(119.32) | 7' | 158.28(157.5) |
| 3' | 28.99(28.5) | 3 | 125.81(124.00) | 4 | 162.38(161.06) |
| 5' | 42.02(41.5) | 6 | 126.26(124.40) | 5 | 162.45(161.43) |
| 2' | 55.80(55.1) | 8a | 134.01(132.98) | 2-COOH | 172.02(165.06) |
| 10a | 116.74(115.83) | 9a | 134.13(133.50) | 1' | 174.87(175.2) |
| 4a | 117.61(118.23) | 7 | 139.08(137.40) | 9 | 183.79(180.47) |
| 1 | 121.50(118.75) | 2 | 147.37(138.18) |  |  |

Note:
The data in the brackets are data of rhein [Carbon-13NMR, Sadtler Division, 1994: 37703C] or arginine [NMR spectral analysis. Analytical Chemistry Handbook (Second Edition, Chemical Industry Press, 1999) volume 7: 909~910]

Comparing the rhein data of conjugate 13C-NMR measuring data with the reported data, the chemical shifts of the C-2 [δ: 147.37(138.18)] and carboxyl carbon-2 [δ:172.02 (165.06)] are about 9 units and 7 units respectively, but the arginine part has the basic group-guanidinium group of medium intensity, therefore, it can be deduced that -cooH-2 of rhein combines with the guanidinium group of arginine to produce salt, see the constitutional formula:

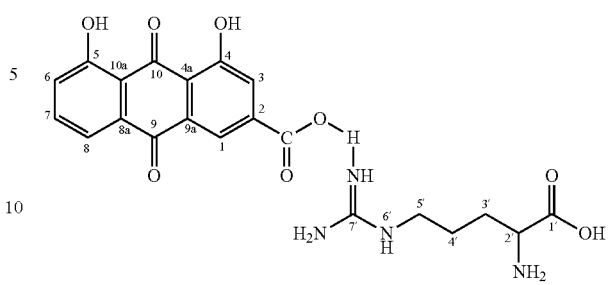

Out of the present invention, the further preferred structure:

1. The left part of formua (I) is rhein-containing effective part, where the content is within 50-99%.

2. The left part of formula (I) is rhein or rhein-containing analogues monomers, where 1~2 substituents of R2-R3, R6-R7 substituents are -COOH, the remaining position of R1~R8 is selected from any of the following: —H, —0-glucose, —OH, —OCH3, —CH3, wherein at least 2 —Hs of R1~R8;

The remaining positions of R1~R8 preferably are selected the following substituents:

| No. | R1 | R2 | R3 | R4 | R5 | R6 | R7 | R8 |
|---|---|---|---|---|---|---|---|---|
| 1 | OH |  | COOH |  |  |  |  | OH |
| 2 | OCH3 | OH | COOH |  |  |  |  |  |
| 3 | OH | OH |  |  |  | COOH | OH |  |
| 4 |  | COOH |  | OH | OH |  | OH |  |
| 5 |  | COOH | OH |  | OH |  |  | OH |
| 6 |  | COOH |  | OH | OH |  | OCH3 |  |
| 7 | OCH3 | OH | COOH |  |  | OCH3 | OCH3 | OH |
| 8 | OCH3 | OH | COOH |  |  | OCH3 | OCH3 | OCH3 |
| 9 | OCH3 | OH | COOH |  |  | OH | OCH3 | OH |
| 10 | OCH3 | OH | COOH |  |  |  |  | OH |
| 11 | OH | COOH | OH |  |  | OCH3 |  | OH |
| 12 | OH | COOH |  |  | OH | OH | OH |  |
| 13 | OCH3 | COOH | OH |  |  |  |  |  |
| 14 | OCH3 | COOH | OH |  |  |  |  |  |
| 15 | OH |  | OH |  |  | COOH |  |  |
| 16 | OH | COOH |  |  |  | OH |  |  |
| 17 | OH | OH | COOH | OH |  |  |  |  |
| 18 | OH |  | COOH |  |  | OCH3 |  | OH |
| 19 | OH | COOH | CH3 |  |  | OH |  | OH |
| 20 | OH | COOH |  |  |  | OH | OH |  |

-continued

| No. | R1 | R2 | R3 | R4 | R5 | R6 | R7 | R8 |
|-----|-----|------|------|------|------|------|------|------|
| 21 | OH | COOH | OH | | | OH | COOH | OH |
| 22 | OH | | COOH | | OH | | | OH |
| 23 | OH | | COOH | OH | | OCH$_3$ | | OH |
| 24 | OH | COOH | | OH | OH | | | OH |
| 25 | OH | | | OH | | | COOH | |
| 26 | OH | | COOH | | | | | |
| 27 | OH | COOH | OH | | | | | |
| 38 | OH | COOH | | OH | OH | | | |
| 29 | OH | COOH | | OH | | | | OH |
| 30 | | OH | | OCH$_3$ | OH | | COOH | |
| 31 | OH | COOH | OH | | OH | | | |
| 32 | | COOH | | | | | | |
| 33 | OH | COOH | | OH | OCH$_3$ | | OH | |
| 34 | OH | COOH | | | OH | | | |
| 35 | OH | COOH | | OH | | | | |
| 36 | OH | OH | OH | | | COOH | | OH |
| 37 | OH | OH | COOH | | | | | OH |
| 38 | OH | | COOH | OH | OH | | | OH |
| 39 | OH | OH | OCH$_3$ | | | COOH | | OH |
| 40 | OH | | OCH$_3$ | | | COOH | OH | |
| 41 | OH | OH | COOH | | | OCH$_3$ | | OH |
| 42 | OH | | COOH | | OH | OCH$_3$ | OH | OH |
| 43 | OH | COOH | OH | | OH | OCH$_3$ | | |
| 44 | OH | | | | | | COOH | |
| 45 | OH | COOH | | | | OH | OCH$_3$ | OCH$_3$ |

The left part of the formula (I) preferably is selected from rhein. 3. In the formula (I), M represents basic amino acid, preferably arginine, lysine or carnitine. 4. In the formula (I) M represents nitrogen-containing organic base, preferably meglumine, glucosamine or ligustrazine.

The process of the preparation of the above rhein or rhein analogues, wherein the rhein-containing effective parts or rhein or rhein analogues monomer reacts with nitrogen-containing organic base or basic amino acids by molar ratio of 1:0.5~4.0 in the water and/or alcohol solvent.

In the aforesaid preparation method, said nitrogen-containing organic base is preferably meglumine, glucosamine or ligustrazine; basic amino acid is preferably arginine, lysine or carnitine.

For the present invention, rhein or rhein analogues reacts with basic amino acid or nitrogen-containing organic base to form medicinal compound, which increases the solubility of rhein orrhein analogues in the water, and can be made into water-carrier pharmaceutical preparations to improve the bioavailability; and the pH value of the solution is more suitable for human body, reducing the stimulation and toxicity.

Rheine or rhein analogues can be extracted from crude drugs or can be synthesized or obtained by other methods.

Rhubarb crude drugs (roots of the same family as Rheum) is pulverized, extracted with water, and then filtered. Inorganic acid and oxidant are added into the water-extracted solution, extracted with organic solvent, and the mixtures (rhein effective parts) is obtained, and then isolated by column chromatography, the rhein monomer is obtained.

Wherein 1:

The preparation of medicinal conjugates by rhein-containing effective parts and basic amino acid or nitrogen-containing organic base comprising:

The obtained rhein-containing effective parts were mixed with water and/or alcohol based on the ratio of 1:0.5~4.0 (mole ratio). The basic amino acid, preferably arginine, lysine or carnitin were added to react with them (mixed evenly while stirring), and the solvent was removed under the conditions of reduced pressure and the preparation was obtained; or the obtained rhein-containing effective parts were mixed with water and/or alcohol based on the ratio of 1:0.5~4.0 (mole ratio), then nitrogen-containing organic base, preferably meglumine, glucosamine or ligustrazine were added to react with them (mixed evenly while stirring), and the solvent was removed under the conditions of reduced pressure and the preparation was obtained.

Wherein 2:

The preparation of medicinal conjugates by rhein monomer and basic amino acid or nitrogen-containing organic base comprising:

The obtained rhein was mixed with water and/or alcohol based on the ratio of 1:0.5~4.0 (mole ratio). The basic amino acid, preferably arginine, lysine or carnitin were added to react with them (mixed evenly while stirring), and the solvent was removed under the conditions of reduced pressure and the preparation was obtained; or the obtained rhein was mixed with water and/or alcohol based on the ratio of 1:0.5~4.0 (mole ratio), then nitrogen-containing organic base, preferably meglumine, glucosamine or ligustrazine were added to react with them (mixed evenly while stirring), and the solvent was removed under the conditions of reduced pressure and the preparation was obtained.

The mixture of the aforesaid rhein or rhein analogues, or the mixture of rhein or rhein analogues was added to pharmaceutic adjuvant to prepare medicinal preparation.

Furthermore, under the present invention, the medicinal compound is formed by rhein-containing effective parts or rhein monomer and basic amino acid or nitrogen-containing organic base. The test results show that the formed conjugate allowed the original water-insoluble rhein-containing effective parts or rhein monomer to become a soluble conjugate, which increased the in vitro dissolution of the oral formulation (suggesting that the in vivo bioavailability of the oral formulation increases); the water-solubility of the conjugate increased and can be made into water-carrier injection. Rhein or rhein analogues sodium salts are strong base weak acid salts in the formulations study, whose aqueous solution presents basicity, and pH value of aqua-puncture is relatively higher, physiologically unacceptable, if lowering the pH value, the preparation has poor stability, see example 49. Under the present invention, the pharmaceutical preparations stability prepared by rhein or rhein analogues conjugate is superior to sodium salt, less irritation, see example 50. Therefore, rhein or rhein analogues conjugate can be used for the treatment of diabetic nephrosis. Metal salts or alkaline-earth metal salts of rhein or rhein compounds, such as sodium salt, potassium salt, calcium salt, magnesium salt also has the functions of treatment of diabetic nephrosis.

In the present invention, various formulations of medicinal combinations can be prepared according to the conventional process of the pharmacy field. For instance, the active ingredient of formula (I) is mixed with one or more carriers, and then made into the required formulations.

To realize the three sub-purposes of the third purpose of the present invention, three options for this invention:

Use of rhein or rhein analogues conjugate for the preparation of drugs of prevention and treatment of diabetic nephrosis;

Use of rhein or rhein analogues conjugate for the preparation of drugs of treatment of osteoarthritis, rheumatic arthritis and rheumatoid arthritis;

Use of rhein or rhein analogues conjugate for the preparation of drugs of treatment of recovery of gastrointestinal function and prevention of intestinal adhesion.

Specifically, the said rhein or rhein analogues conjugate can be used as the raw materials of effective ingredient of drugs, and then combined with the pharmaceutic adjuvant acceptable in the pharmacy to prepare for the medical combination of prevention and treatment of diabetic nephrosis, which contains any of the aforesaid rhein or rhein analogues conjugate and the pharmaceutical acceptable carriers.

Either of the above rhein or rhein analogues conjugates, or mixture of rhein or rhein analogues conjugates was added into pharmaceutic adjuvant to prepare pharmaceutical preparation for the use of preparation of drug in the treatment of diabetic nephrosis. Said medical combination is any of formulations in the pharmacy, including tablets, capsules, soft capsules, gels, oral agent, suspension, preparation for infusion, patch, cream, pills, powders, injection, infusion solutions, freeze-dried injection, intravenous emulsion, liposome injection, suppository, or sustained-release preparation or controlled release preparation.

In the present invention, the medicinal combination preferably selects the mixture of the formula (I) conjugate and any of rhein analogues by an arbitrary proportion, wherein the content of rhein analogues ranges from 1% to 95%.

The medicinal combination preferably selects the formula (I) conjugate of molar ratio of 0.1%-99.5%, wherein the content of rhein analogues ranges from 1o % to 95%.

The medicinal combination, in addition to containing the active ingredients of the above formula (I) conjugate and rhein analogues of effective content, also contains one or more kinds of pharmaceutical acceptable carriers.

The pharmaceutical acceptable carriers hereinabove refer to the conventional drug carriers in the pharmacy fields, such as diluent, water and excipient, etc, fillers such as starch, sucrose, lactose and microcrystalline cellulose, etc; adhesives such as cellulose derivatives, alginate, gelatin and polyvinylpyrrolidone; wetting agent such as glycerol; disintegrating agents such as sodium carboxymethyl starch, hydroxypropyl cellulose, cross-linked carboxymethyl cellulose, agar, calcium carbonate and sodium bicarbonate; absorption enhancers such as quaternary ammonium compounds; surfactants such as palmityl alcohol, sodium dodecylsulfate; adsorption carriers such as kaolin and bentonite; lubricants such as talc powder, calcium stearate and magnesium stearate, Gum Acacia and polyethylene glycol, etc. In addition, other auxiliary agents such as flavor agent and sweeting agent can be added into the combination.

The medicinal combination can be applied to the patients for treatment through oral, rectal or parenteral administration. For oral administration, the medicinal combination can be made into conventional formulations such as tablets, capsules, powders, granules, etc., made into liquid formulations such as water or oil suspending agent or other liquid preparations such as syrup, oral solution, elixir, etc; for parenteral administration, can be made into injection solution, powder acupuncture, water or oil suspending agent, etc. The preferable forms are tablets, coated tablets, capsules, granules, oral liquid and injection.

One aspect of the present invention is a medical combination preparation comprising of any one of the following preparations, including tablets, capsules, soft capsules, sprays, gels, gel inhalation agent, oral agent, suspension, preparation for infusion, patch, cream, pills, powders, injection, infusion solutions, freeze-dried injection, intravenous emulsion, liposome injection, targeted drug delivery injection, suppository, or sustained-release preparation or controlled release preparation.

Another aspect of this invention is said medical combination preparation is the tablets or capsules combined by medicinal composition comprising rhein analogues and rhein analogues and different basic groups or ions, filling agent and disintegrating agent; or the sustained-release tablets or capsules combined by medicinal composition comprising rhein analogues and rhein analogues and different basic groups or ions, filling agent and hydroxypropyl methy cellulose K4M; or rhein analogues soft capsules dispersed in the oil phase of rhein compound.

Yet another aspect of this invention is said medical combination preparation wherein said filling agent is sucrose, lactose and microcrystalline cellulose, dextrin, starch or calcium phosphate; said disintegrating agent is hydroxypropylcellulose, sodium carboxymethyl starch, polyvinylpolypyrrolidone or sodium carboxymethyl cellulose;

Yet another aspect of this invention is said medical combination preparation contains adhesives, moistening agents or lubricants.

Yet another aspect of this invention is said medical combination preparation is the injection formed by rhein analogues and solubilizer or solvent; or freeze-dried injectable power acupuncture agent; or injectable emulsion dispersed in the oil phase of rhein compounds, or suspending injection solution. Said suspending injection solution is obtained by mixing rhein analogues tiny powder and polysorbate 80 and grinding them, then dissolving in the aqueous solution consisting of potassium dihydrogen phosphate, dipotassium hydrogen phosphate, nipagin ester and sodium carboxymethyl cellulose, then grinding.

Yet another aspect of this invention is said medical combination preparation wherein said oil phase consisting of soybean oil, polyethylene glycol 400, cottonseed oil, peanut oil, sesame oil, corn oil or olive oil; wherein said oil phase can be added into solubilizers or cosolvents or anti oxidants.

Yet another aspect of this invention is said medical combination preparation wherein said solubilizer consisting of polyoxyethylene castor oil, polyoxyethylene hydrogenated castor oil, polyoxyethylene pyrrolidone, poloxamer, tween, polyethylene glycol, pluronic F-68; wherein said cosolvents consisting of arginine, lysine, meglumine or glucosamine, diethylamine, ethylenediamine, urea, carnitine, ligustrazine, nicotinamide, proline, glucose and citric acid and its sodium salt.

Yet another aspect of this invention is said process of various formulations of medicinal combination preparation, wherein active ingredients of rhein analogues or rhein analogues conjugate are mixed with one or more kinds of carriers, then made into the required preparations.

Said medicinal combination is preferably selected from active ingredients of rhein analogues or rhein analogues conjugate of weight ratio ranging from 0.1% to 99.5%, more preferably selected from active ingredients of rhein analogues or rhein analogues conjugate of weight ratio ranging from 0.5% to 95%.

The use of medicinal combination of formula (I) may be changed according to the administration routes, patient's age, weight and body surface area, the types of treated diseases and severity, etc, and the daily dosage can be 1-300 mg/m2 adult's body surface area, preferably 10-200 mg/m2 adult's body surface area, which can be administered once or more times.

The examples below are designed to demonstrate but not limit the embodiments of the present invention.

In the present invention, various kinds of preparations of medicinal combination can be prepared according to the conventional production methods of the pharmacy field. For instance, mix compound of formula (I) or rhein analogues with one or more kinds of carriers, then prepare the required preparations.

In the present invention, rhein or rhein analogues conjugates overcome the deficiencies of low solubility, non-medicinal use of rhein or rhein analogues, and higher pH value, unstable aqua-acupuncture, unacceptable for human body of strong base salt of rhein analogues. Rhein or rhein analogues conjugates can not only increase its water solubility, but also can be prepared into various kinds of medicinal preparation, especially the water-carrier preparations, convenient for use; the present invention also relates to a process of preparation of medicinal conjugates by aforesaid rhein analogues and basic amino acid or different basic groups. The present invention still relates to the use of said conjugates for the preparation of drugs in the treatment of diabetic nephritis. The conjugates are weak acid weak base conjugates, solution is close to neutral, and the injection or oral liquid solution is also close to neutral, easily to be acceptable in the medical study, having better compliance in human body. The stability of preparation is superior to sodium and potassium salts, less irritation of its aqua acupuncture, so it can be used to prepare the drugs for treatment of diabetic nephrosis. Currently, most of listed products and literature relate to rhubarb medicinal herbs and its compound preparation or rhubarb extracts, and no reports concerning rhein or rhein analogues-containing effective parts and basic amino acid or nitrogen-containing organic base conjugates can be found in the literature, even no listed medicines, therefore, the present invention initially discloses rhein or rhein analogues conjugates and the process, combination and use of preparation of drugs.

DESCRIPTION OF DRAWINGS

FIG. 1 Rhein arginine elemental analysis test report;

FIG. 3, FIG. 4 13C-NMR spectroscopy of rhein arginine conjugates

DETAILED DESCRIPTION OF THE INVENTION

Figure 2:
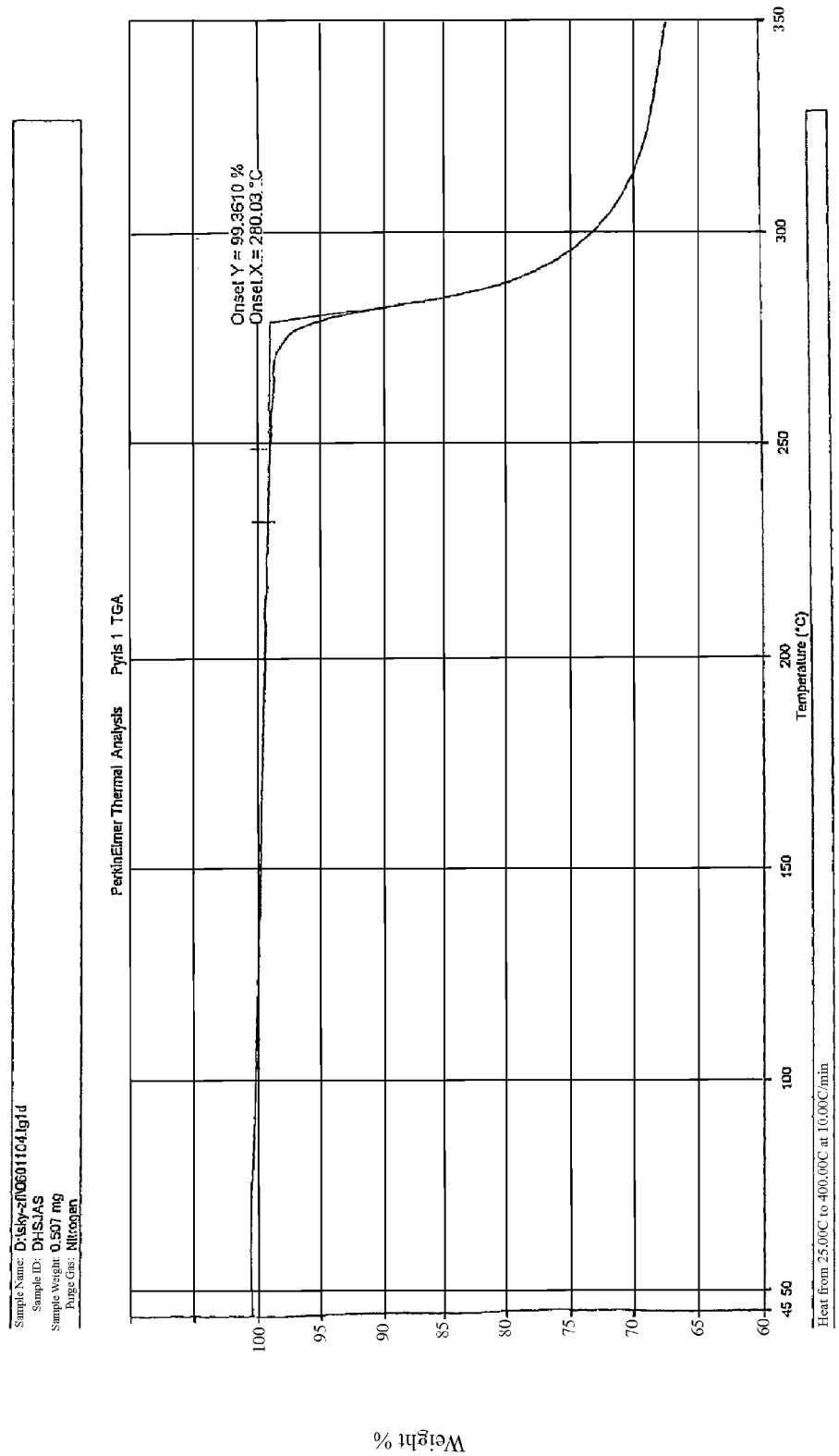
FIG. 2 Rhein arginine conjugates gravitational thermal analysis (GTA) Spectrum
Figure 3:
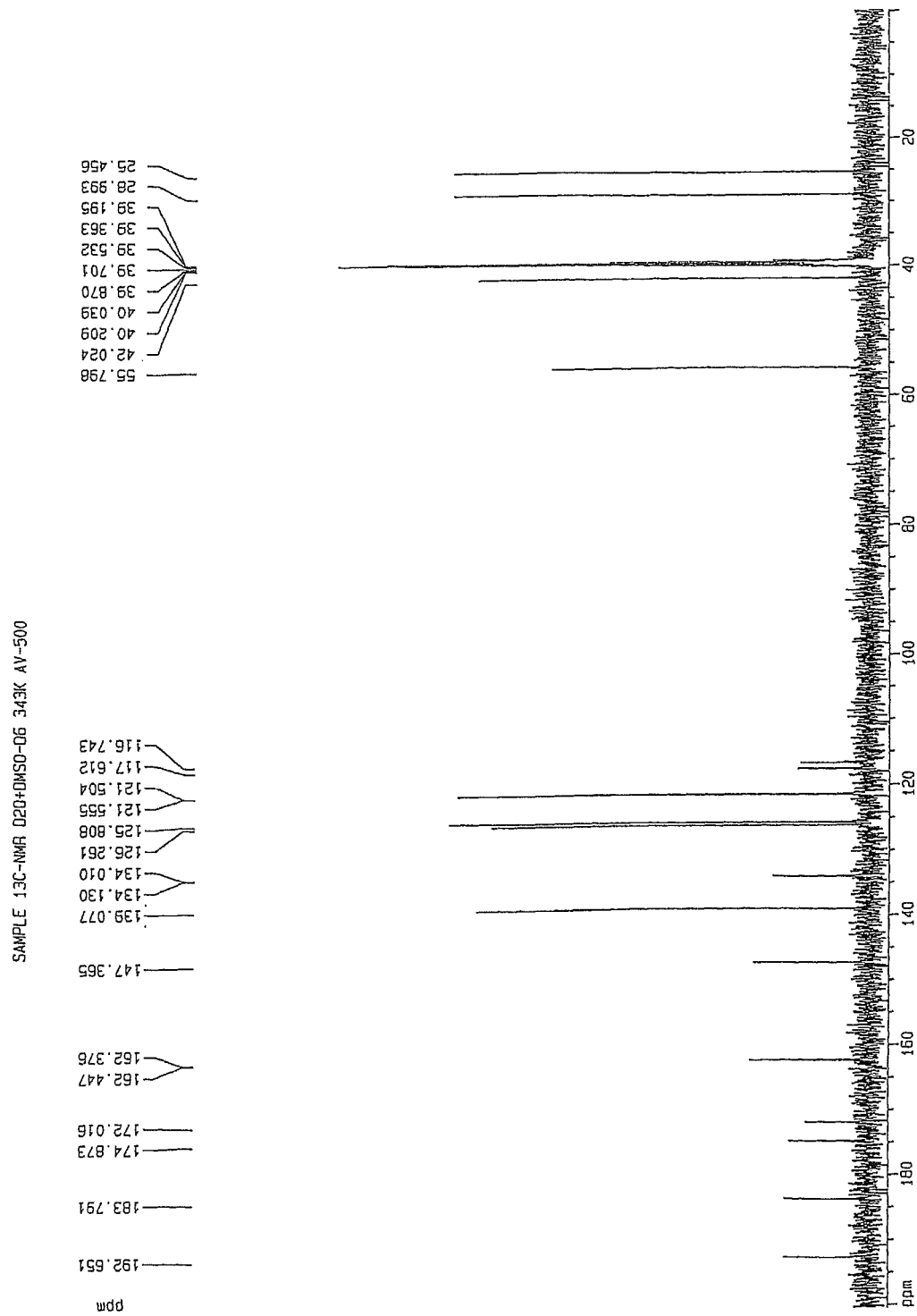
Figure 4:
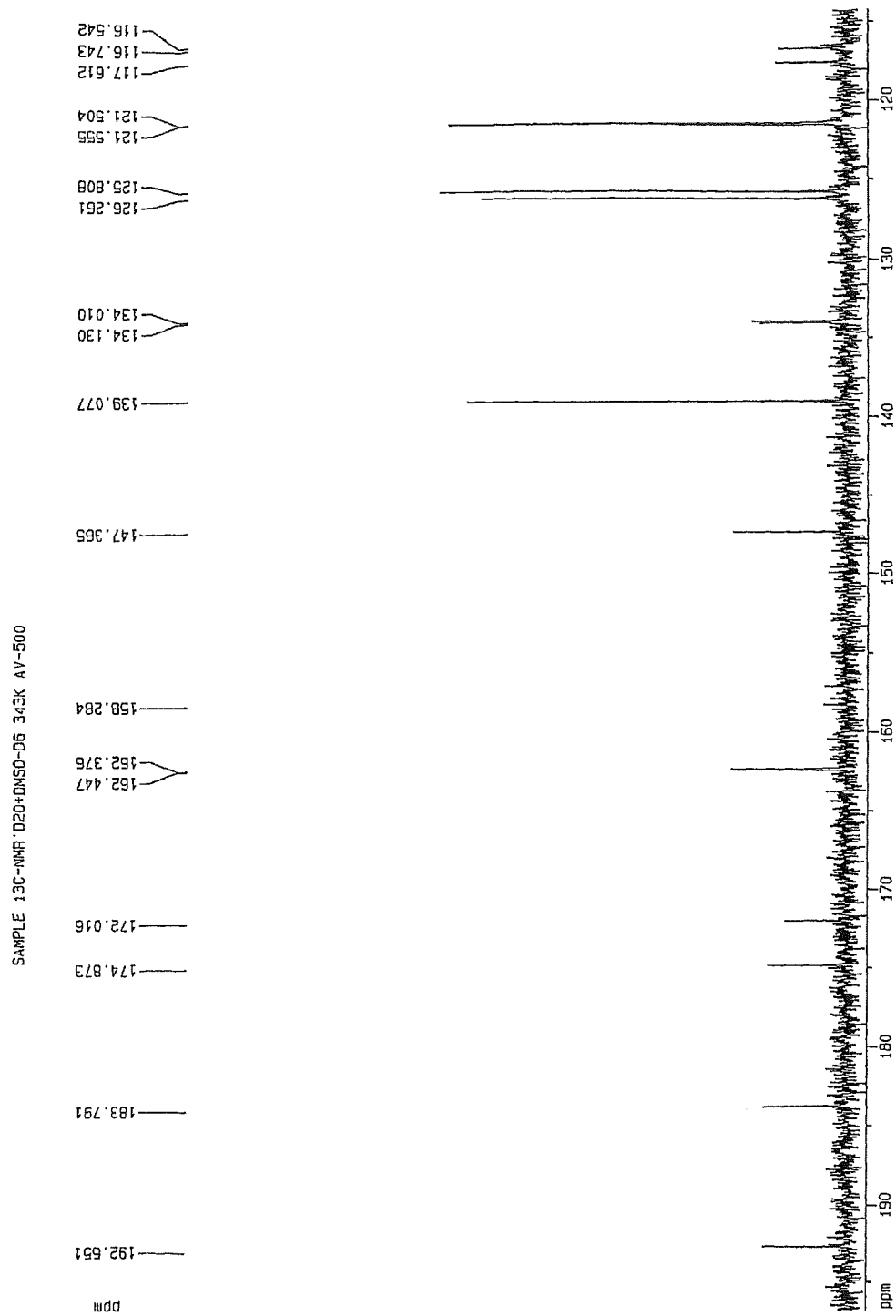

Example 1 Extraction and Purification of Rhein 500 g of rhubarb powder was added into five times of amount of 60% ethanol, heated and refluxed twice, one hour for each time. The extraction solution was merged and concentrated into about 1000 ml, then added with 100 ml of concentrated hydrochloric acid for hydrolyzing 1 hour under 50° C., cooled and filtered it to obtain the precipitation. Then the resulting mixture was added with 1000 ml of 5% NaHCO3 solution, heated to dissolve, filtered, then ethanol was added to the filtrate to allow concentration of ethanol to 50~90%, filtered, adjusted the pH value of the filtrate to below 3 with concentrated hydrochloric acid, filtered again to obtain yellow precipitation. The reaction mixture was washed with water to neutral; recrystallized with glacial acetic acid to obtain rhen. The product yield was above 98%.

Example 2 Preparation of Rhein 6 g of chrysophanol was added to 150 ml of mixed solution of anhydride and pyridine (1:1), overnight at room temperature. The reaction mixture was put into cold water for crystallization, then filtered and dried, was put into 300 ml of acetic anhydride and glacial acetic acid mixture (1:1). Chromium trioxide solution was dropped at 45° C., and then was stirred for 8 hours at 65° C. The reaction mixture was put into water, crystallized, filtered, added into 1000 ml of 25% sodium carbonate solution, extracted by chloroform for three times. Sodium carbonate solution was heated to boiling, cooled, added into hydrochloric acid for acidification. Until a large amount of gas is drained off, the solution was heated to boiling for 1 hour, cooled, crystallized, filtered and washed by water, recrystallized with glacial acetic acid, thus 2 g of rhein was obtained. The product yield was above 98%.

Example 3 Preparation of 50% Rhein-containing Effective Part 100 g of rhubarb powder was added into five times amount of 60% ethanol, heated and refluxed for hydrolysis for 1 hour, filtered. The filtrate was mergered and concentrated under reduced pressure into 30% of the volume of the original solution, and a thin syrup substance was obtained. Concentrated hydrochloric acid (1 concentrated hydrochloric acid/10 times of medicinal materials) was added while it was hot, stirred for more than 10 min, centrifuged and the precipitate was obtained. The same amount of 5% sodium bicarbonate as the concentrated solution was added, heated to dissolve, centrifuged. The supernatant was collected and added into ethanol to allow ethanol content of 60~90%, then stirred, centrifuged and the supernatant was collected, added into concentrated hydrochloric acid to adjust the pH value to below 2, centrifuged, and dried, and the brown powder was obtained.

Example 4 Preparation of Arginine Conjugate of 50% Rhein-containing Effective Part 40 g of 50% rhein-containing effective part was put into a suitable container, then water was added, and 22 g L-arginine was added, heated and cooled, then added into ethanol to allow the content of ethanol of 60~90%, after then, stirred to dissolve, filtered, and the filtrate was concentrated. Ethanol was added into the concentrated solution to allow ethanol content ranging from 40% to 80%, placed still, filtered and dried to obtain 28 g of solid.

Example 5 Preparation of Lysine Conjugate of 50% Rhein-containing Effective Part 40 g of 50% rhein-containing effective part was put into a suitable container, then water was added, and 20 g L-lysine was added, heated and cooled, then added into ethanol to allow the content of ethanol of 50~90%, after then, stirred to dissolve, filtered, and the filtrate was concentrated. Ethanol was added into the concentrated solution to allow ethanol content ranging from 40% to 80%, placed still, filtered and dried to obtain 25 g of solid.

Example 6 Preparation of Rhein Arginine Conjugate 2 g of rhein was put into a suitable container, added with ethanol to dissolve. 2.5 g of L-arginine was dissolved in water and then added into rhein solution, heated, dissolved under stirring and extracted the solvent under reduced pressure, and 3.1 g of solid was obtained.

Example 7 Preparation of Rhein Lysine Conjugate 2 g of rhein was put into a suitable container, added with ethanol to dissolve. 2.3 g of lysine was dissolved in water and then added into rhein solution, heated, dissolved under stirring and extracted the solvent under reduced pressure, and 2.9 g of solid was obtained.

Example 8 Preparation of Rhein Meglumine Conjugate 2 g of rhein was put into a suitable container, added with ethanol to dissolve. 3 g of meglumine was dissolved in water and then added into rhein solution, heated, dissolved under stirring and extracted the solvent under reduced pressure, and 3.1 g of solid was obtained.

Example 9 Preparation of Rhein Carnitine Conjugate 2 g of rhein was put into a suitable container, added with ethanol to dissolve. 2.5 g of carnitine was dissolved in water and then added to rhein solution, heated, dissolved under stirring and extracted the solvent under reduced pressure, and 3 g of solid was obtained.

EXAMPLE 10 Preparation of Rhein Ligustrazine Conjugate 2 g of rhein was put into a suitable container, added with ethanol to dissolve. 2.3 g of ligustrazine was dissolved in water and then added to rhein solution, heated, dissolved under stirring and extracted the solvent under reduced pressure, and 2.6 g of solid was obtained.

Example 11 Preparation of Rhein Glucosamine Conjugate 6.3 g of glucosamine was dissolved in 250 ml of distilled water, added with 2.5 g of rhein under constant stirring, heated and refluxed for 2 hours. The resulting mixture was slightly cooled, added with 700 ml of anhydrous alcohol, centrifuged and separated, and the precipitation was abandoned. Part of solvent of the supernatant was steamed under reduced pressure until the remaining volume of 1000 ml. The resulting mixture was added with 70 ml of anhydrous alcohol, cooled, and yellow solid substance was separated out, and then filtered. The filter cake was recrystallized by aqueous ethanol, dried at 40.degree.C. under vacuum, and rhein glucosamine was obtained.

Example 12 Preparation of Glucosamine Conjugate of 50% Rhein-containing Effective Part 6.3 g of glucosamine was dissolved in 250 ml of distilled water, added with 5 g of 50% rhein-containing effective part under constant stirring, heated and refluxed for 2 hours. The resulting mixture was slightly cooled, added with 700 ml of anhydrous alcohol, centrifuged and separated, and the precipitation was abandoned. Part of solvent of the supernatant was steamed under reduced pressure until the remaining volume of about 100 ml. The resulting mixture was added with 70 ml of anhydrous alcohol, cooled, and yellow solid substance was separated out, and then filtered, dried at 30-60.degree. C. under vacuum, and glucosamine conjugate of 50% rhein-containing effective part was obtained.

Example 13 Preparation of Carnitine Conjugates of 50% Rhein-containing Effective Part 40 g of 50% rhein-containing effective part was put into a suitable container, added with water, and then added with 22 g of carnitine. The resulting mixture was heated, cooled, and added with ethanol to allow the content of ethanol content up to 50~90%, then stirred evenly till dissolved, and filtered. The filtrate was concentrated. The concentrated solution was added with ethanol to allow the content of ethanol up to 40-80%. The resulting mixture was placed still, filtered and dried, and 27 g of solid substance was obtained.

Example 14 Preparation of Meglumine Conjugate of 50% Rhein-containing Effective Part 40 g of 50% rhein-containing effective part was put into a suitable container, added with water, and then added with 27 g of meglumine. The resulting mixture was heated, cooled, and added with ethanol to allow the content of ethanol content up to 50~90%, then stirred evenly till dissolved, and filtered. The filtrate was concentrated. The concentrated solution was added with ethanol to allow the content of ethanol up to 40-80%. The resulting mixture was placed still, filtered and dried, and 27 g of solid substance was obtained.

Example 15 Preparation of Ligustrazine Conjugate of 50% Rhein-containing Effective Part 40 g of 50% rhein-containing effective part was put into a suitable container, added with water, and then added with 25 g of ligustrazine. The resulting mixture was heated, cooled, and added with ethanol to allow the content of ethanol content up to 50~90%, then stirred evenly till dissolved, and filtered. The filtrate was concentrated. The concentrated solution was added with ethanol to allow the content of ethanol up to 40-80%. The resulting mixture was placed still, filtered and dried, and 30 g of solid substance was obtained.

Example 16 Preparation of 4,5,7-trihydroxy-2carboxyanthraquinone 6 g of emodin was added into 200 ml of mixed solution of anhydride and pyridine (1:1), overnight at room temperature. The reaction mixture was put into cold water for crystallization, then filtered and dried, put into 300 ml of acetic anhydride and glacial acetic acid mixture (1:1). Chromium trioxide solution was instilled at 45° C. while constant stirring for 8 hours at 65° C. The reaction mixture was put into water, crystallized, filtered, added into 1000 ml of 25% sodium carbonate solution, extracted by chloroform for three times. Sodium carbonate solution was heated to boiling, cooled, and added with hydrochloric acid for acidification. Until a large amount of gas is drained off, the solution was heated to boiling for 1 hour, cooled, crystallized, filtered and washed by water, recrystallized with glacial acetic acid, thus 1.9 g of 4,5,7-trihydroxy-2-carboxyanthraquinone was obtained. The product yield was above 98%.

Example 17 Preparation of 1,3-dihydroxy-6-carboxyanthraquinone 6 g of 6-methyl rubiadin was added, the procedure is carried out as Example 16, and 2 g of 1,3-dihydroxy-6-carboxyanthraquinone was obtained.

Example 18 Preparation of 4,5,7-trihydroxy-2-carboxyanthraquinone Lysine Conjugate 2 g of 4,5,7-trihydroxy-2-carboxyanthraquinone was put into a suitable container, added with ethanol to dissolve. 2.5 g of L-arginine was dissolved in water and then added to rhein solution, heated, dissolved under stirring and extracted the solvent under reduced pressure, and solid substance of 4,5,7-trihydroxy-2-carboxyanthraquinone arginine conjugate was obtained.

Example 19 Preparation of 4,5,7-trihydroxy-2-carboxyanthraquinone Lysine Conjugate 2 g of 4,5,7- trihydroxy-2-carboxyanthraquinone was put into a suitable container, added with ethanol to dissolve. 2.2 g of L-lysine was dissolved in water and then added to rhein solution, heated, dissolved under stirring and extracted the solvent under reduced pressure, and solid substance of 4,5,7-trihydroxy-2-carboxyanthraquinone lysine conjugate was obtained.

Example 20 Preparation of 4,5,7-dihydroxy-2-carboxyanthraquinone Glucosamine Conjugate The procedure was carried out basically as Example 11, but, wherein rhein should be replaced by 4,5,7- trihydroxy-2-carboxyanthraquinone.

Example 21 Preparation of 4,5,7- trihydroxy-2-carboxyanthraquinone Meglumine Conjugate The procedure was carried out basically as Example 8, but, wherein rhein should be replaced by 4,5,7-trihydroxy-2-carboxyanthraquinone.

Example 22 Preparation of 4,5,7-dihydroxy-2-carboxyanthraquinone Carnitine Conjugate The procedure was carried out basically as Example 9, but, wherein rhein should be replaced by 4,5,7-trihydroxy-2-carboxyanthraquinone.

Example 23 Preparation of 4,5,7-dihydroxy-2-carboxyanthraquinone Ligustrazine Conjugate The procedure was carried out basically as Example 10, but, wherein rhein should be replaced by 4,5,7- trihydroxy-2-carboxyanthraquinone.

The conjugates prepared under Example 4~15, 18~23 were used as the drugs for treatment of diabetic nephrosis respectively.

The conjugates prepared under Example 4~15, 18~23 were used as the drugs for treatment of recovery of gastrointestinal function and prevention of intestinal adhesion respectively.

The conjugates prepared under Example 4~15, 18~23 were used as the drugs for treatment of osteoarthritis, rheumatic arthritis and rheumatoid arthritis respectively.

Example 24 Preparation of Rhein or Rhein-containing Effective Part Capsules

| | |
|---|---|
| rhein or rhein-containing effective part (calculated by rhein) | 20 g |
| microcrystalline cellulose | 60 g |
| lactose | 100 g |
| sodium carboxymethyl starch | 14 g |
| 2% HPMCE5 solution | proper amount |
| 6% tween 80 | proper amount |
| magnesium stearate | 2 g |

Rhein or rhein-containing effective part, microcrystalline cellulose, lactose and sodium carboxymethyl starch were passed through 100 mesh sieves and mixed evenly. HPMG solution containing tween 80 was used as adhesive soft material. After passing through 20 mesh sieves, the wet particles were dried by air blasting through drying oven at 50-60° C.; and the dried particles were passed through 20 mesh sieves, mixed evenly with magnesium stearate and filled in the capsules.

Example 25 Preparation of Rhein or Rhein-containing Effective Part Conjugate Capsules

| | |
|---|---|
| rhein or rhein-containing effective part conjugate (material-feeding was calculated by rhein, the same below) | 20 g |
| microcrystalline cellulose | 30 g |
| lactose | 30 g |
| sodium carboxymethyl starch | 5 g |
| 2% HPMCE5 solution | proper amount |
| 6% tween 80 | proper amount |
| magnesium stearate | 1 g |

Rhein or rhein-containing conjugate, microcrystalline cellulose, lactose and sodium carboxymethyl starch were passed through 100 mesh sieves separately and mixed evenly. HPMC solution containing tween 80 was used as adhesive soft material. After passing through 20 mesh sieves, the wet particles were dried by air blasting through drying oven at 50-60° C.; and the dried particles were passed through 20 mesh sieves, mixed evenly with magnesium stearate and filled in the capsules.

Example 26 Preparation of Rhein or Rhein-containing Effective Part Tablets

| | |
|---|---|
| rhein or rhein-containing effective part | 20 g |
| microcrystalline cellulose | 30 g |
| lactose | 40 g |
| sodium carboxymethyl starch | 7 g |
| 2% HPMCE5 solution | proper amount |
| 5% tween 80 | proper amount |
| magnesium stearate | 1 g |

Rhein or rhein-containing effective part, microcrystalline cellulose, lactose and sodium carboxymethyl starch were passed through 100 mesh sieves separately and mixed evenly. HPMC solution containing tween 80 was used as adhesive soft material. After passing through 20 mesh sieves, the wet particles were dried by air blasting through drying oven at 50-60° C.; and the dried particles were passed through 20 mesh sieves, mixed evenly with magnesium stearate and pressed into tablets.

Example 27 Preparation of Rhein or Rhein-containing Effective Part Conjugate Tablets

| | |
|---|---|
| rhein or rhein-containing effective part conjugate (material-feeding was calculated by rhein, the same below) | 20 g |
| microcrystalline cellulose | 30 g |
| lactose | 40 g |
| sodium carboxymethyl starch | 5 g |
| 2% HPMCE5 solution | proper amount |
| 6% tween 80 | proper amount |
| magnesium stearate | 1 g |

Rhein or rhein-containing effective part conjugate, microcrystalline cellulose, lactose and sodium carboxymethyl starch were passed through 100 mesh sieves separately and mixed evenly. HPMC solution containing tween 80 was used as adhesive soft material. After passing through 20 mesh sieves, the wet particles were dried by air blasting through drying oven at 50-60° C.; and the dried particles were passed through 20 mesh sieves, mixed evenly with magnesium stearate and pressed into tablets.

Example 28 Preparation of Rhein or Rhein-containing Effective Part Conjugate Enteric-coated Tablets Rhein or rhein-containing effective part conjugate was dried, added with starch, mixed evenly. The resulting mixture was prepared into granules with 0.5% camphor oil dilute alcohol solution, dried, and pressed into 1000 tablets. Acrylic acid 2 was used and added with castor oil, mixed, then added with 95% ethanol till 600 ml. Finally coating was carried on by spray turnadle pan coating method.

Example 29 Preparation of Rhein or Rhein-containing Effective Part Conjugate Enteric-coated Capsules Rhein or rhein-containing effective part conjugate and cellulose acetate phthalate CAP 209 were dissolved into the 500 ml of acetone and ethanol (1:1) mixture solution. The resulting mixture was slowly infused with n-hexane while stirring until the precipitation produced. Then the reaction mixture was hardened, dried, and then enteric-coated microcapsules were loaded into ordinary hollow hard capsules, and enteric-coated capsules were made.

Example 30 Preparation of Rhein or Rhein-containing Effective Part Sustained Release Capsules

| rhein or rhein-containing effective part | 50 g |
|---|---|
| polyvidone | 50 g |
| microcrystalline cellulose | 15 g |
| hypromellose K4M | 50 g |
| 3% hypromellose (E5) aqueous solution | proper amount |
| Talc Powder | 2 g |

Rhein or rhein-containing effective part and polyvidone was dissolved into small amount of ethanol, and heated under reduced pressure to evaporate ethanol. The resulting solid was passed through 100 mesh sieve; the above solid and microcrystalline cellulose, hypromellose K4M were passed through 60 mesh sieve, and added with proper amount of 3% hypromellose (E5) aqueous solution to made soft materials, then passed through 20 mesh sieve to made granules. Then dried by air blasting of drying oven at 40-50° C.; the dry granules were passed through 20 mesh sieve for size stabilization, added with talcum powder according to the prescription, mixed evenly, and then filled into capsules according to the prescription.

Example 31 Preparation of Rhein or Rhein-containing Effective Part Conjugate Sustained Release Capsules

| rhein or rhein-containing effective part conjugate (material-feeding was calculated by rhein, the same below) | 80 g |
|---|---|
| microcrystalline cellulose | 15 g |
| hypromellose K4M | 100 g |
| 3% hypromellose (E5) aqueous solution | proper amount |
| talc powder | 2 g |

Rhein or rhein-containing conjugate, microcrystalline cellulose, hypromellose K4M were passed through 60 mesh sieves and mixed evenly, and added with proper amount of 3% hypromellose (E5) aqueous solution to made soft materials, then passed through 20 mesh sieve to made granules. Then dried by air blasting of drying oven at 40-50° C. The dry granules were passed through 20 mesh sieves for size stabilization, and added with talcum powder according to the prescription, mixed evenly, and then filled into capsules according to the prescription.

Example 32 Preparation of Rhein or Rhein-containing Effective Part Sustained Release Capsules

| rhein or rhein-containing effective part | 50 g |
|---|---|
| polyvidone | 50 g |
| lactose | 15 g |
| hypromellose K4M | 100 g |
| 3% hypromellose (E5) aqueous solution | proper amount |
| talc powder | 1 g |

Rhein or rhein-containing effective part and polyvidone was dissolved into small amount of ethanol, and heated under reduced pressure to evaporate ethanol. The resulting solid was passed through 100 mesh sieve; the above solid and lactose, hypromellose K4M were passed through 60 mesh sieve and mixed evenly, and added with proper amount of 3% hypromellose (E5) aqueous solution to made soft materials, then passed through 20 mesh sieve to made granules. Then dried by air blasting under a drying oven at 40-50° C.; the dried granules were passed through 20 mesh sieve for size stabilization, and added with talcum powder according to the prescription, mixed evenly, and then pressed tablets.

Example 33 Preparation of Rhein or Rhein-containing Effective Part Conjugate Sustained Release Capsules

| rhein or rhein-containing effective part conjugate (material-feeding was calculated by rhein, the same below) | 80 g |
|---|---|
| lactose | 15 g |
| hypromellose K4M | 100 g |
| 3% hypromellose (E5) aqueous solution | proper amount |
| talc powder | 2 g |

Rhein or rhein-containing effective part, lactose, hypromellose K4M were passed through 60 mesh sieve and mixed evenly, and added with proper amount of 3% hypromellose (E5) aqueous solution to made soft materials, then passed through 20 mesh sieve to made granules. Then dried by air blasting under a drying oven at 40-50° C.; the dried granules were passed through 20 mesh sieve for size stabilization, and added with talcum powder according to the prescription, mixed evenly, and then pressed tablets.

For the above examples, other adjuvants can be selected, disintegrating agents, such as: hydroxypropyl starch, hydroxypropyl cellulose, sodium carboxymethyl starch, carboxymethyl cellulose calcium, dextrin, starch, calcium phosphate, calcium hydrogen phosphate, calcium sulfate, calcium carbonate, cyclodextrin, microcrystalline cellulose, etc; wetting agent and adhesives, such as amylum pregelatinisatum, polyvidone, sodium carboxymethyl cellulose, hypromellose; lubricants such as: talc powder, stearic acid, magnesium stearate, calcium stearate, fine silica gel, hydrogenated vegetable oil, polyethylene glycol 4000 and 6000; wetting agents, such as: sodium dodecylsulfate, tween 80; framing materials such as hypromellose, ethylcellulose, etc.

Example 34 Preparation of Rhein or Rhein-containing Effective Part Soft Capsules

| content | content/pill | capsule shell | |
|---|---|---|---|
| rhein or rhein-containing effective part | 50 mg | gelatin | 46.00% |
| soybean oil | 0.5 ml | glycerol | 17.82% |
| | | water | 36.18% |

Rhein or rhein-containing effective part were dissolved in the soybean oil, and the resulting mixture solution was made into soft capsules. Each pill contained rhein or total rhein of 50 mg.

In this example, the soft capsule may be selected from the following adjuvants: solvents such as: polyethylene glycol 400, cottonseed oil, peanut oil, sesame oil, corn oil, olive oil, etc.; solubilizers or cosolvents, such as tween 80, polyoxyethylene castor oil, benzyl benzoate, ethyl lactate, ethyl oleate, phospholipid, etc; antioxidants, such as: propyl gallate, t-butyl phenol (BHT), vitamin E, etc. For the capsule shell, the proportion of gelatin, glycerin and water can be properly adjusted, for instance, the ratio of gelatin/glycerol/water of 1:0.3~0.4:0.7~1.4 is applicable. Other ingredients can be added into the capsule shell, such preservatives: such as: methyl-p-hydroxybenzoate, ethyl ρ-hydroxybenzoate, propyl parahydroxy benzoate, butyl p-hydroxybenzoate, etc; Plasticizers such as sorbitol, etc; stabilizer such as arabic gum, etc; sun-screening agents, such as: titanium dioxide, barium sulfate, precipitated calcium carbonate, etc.

Example 35 Preparation of Rhein or Rhein-containing Effective Part Injectable Emulsions

| rhein or rhein-containing effective part | 20 g |
|---|---|
| soybean oil | 50 g |
| soybean phospholipid | 12 g |
| glycerol | 25 g |
| add injectable water till | 10000 ml |

Under the condition of nitrogen flow, soybean phospholipid was added into soybean oil and mixed to dissolve, then glycerol and rhein or rhein-containing effective part were added and dissolved while stirring. Under constant stirring, injectable water was slowly added, and emulsified by two-step high-pressure emulsifier; and still under the condition of nitrogen flow, the resulting mixture was filtered by No. 4 sintered glass funnel under reduced pressure, and carried on bottle filling and lid rolling. Then preheated and sterilized for 15 minutes at 121° C., after sterilization is completed, spraying hot water and gradually cooling it down.

In this example, the following adjuvants can be selected: injectable oil, such as: ethyl oleate, polyethylene glycol 400, cottonseed oil, peanut oil, sesame oil, corn oil, olive oil, isopropyl myristate, etc; antioxidants such as: propyl gallate, t-butyl phenol (BHT), vitamin E, etc; surfactants such as: tweens, polyoxyethylated castor oil, phospholipids, pluronic etc.

Example 36 Preparation of Rhein or Rhein-containing Effective Part Conjugate Injections

| rhein or rhein-containing effective part conjugate (calculated by rhein) | 10 g |
|---|---|
| add injectable water till | 5 L |

Rhein or rhein-containing effective part conjugate was added into injectable water to fully dissolve, then added with 0.1% activated carbon, heated to boiling for 15 minutes. The resulting mixture was filtered to remove surface substance, adjusted the pH values ranging from 5.0 to 7.0. Then intermediate content, pH value were measured, when qualified, the mixture was filled and sealed them into a glass ampule, then carried on circulation steam sterilization for 30 minutes at 100° C., and rhein or rhein-containing effective part conjugate injection was obtained.

Example 37 Preparation of Rhein or Rhein-containing Effective Part Injections

| rhein or rhein-containing effective part | 10.0 g |
|---|---|
| arginine or lysine | 6.2 g |
| sodium chloride | proper amount |
| add injectable water till | 10000 mL |

Rhein or rhein-containing effective part and arginine or lysine (or conjugate) were put into a suitable container, added with 9000 ml of injectable water and mixed evenly, then dissolved by ultrasound wave, then added with sodium chloride to dissolve while stirring, supplemented injectable water to 10000 ml. The resulting mixture was filtered through 0.22 μm microporous membranes, filled and sealed, then sterilized by flowing steam for 30 minutes at 100° C.

Example 38 Preparation of Rhein or Rhein-containing Effective Part Injectable Powder

| rhein or rhein-containing effective part | 10.0 g |
|---|---|
| arginine or lysine | 6.2 g |
| mannitol | 16.0 g |
| add injectable water till | 10000 mL |

Rhein or rhein-containing effective part and arginine or lysine were put into a suitable container, added with 9000 ml of injectable water and mixed evenly, then dissolved by ultrasound wave, then added with mannitol to dissolve while stirring; added with 0.1% injectable active carbon with 30 minutes of stirring, decarbonized and suctioned into a clean container through titanium sand core, supplemented injectable water to 10000 ml, mixed evenly for five minutes, and then filtered through 0.22 μm microporous membranes and the filtrate was filled into cillin bottles with 2 ml or 5 ml in one bottle, and then partially plugged with rubber stopper and sent onto the lamination plate in the freeze-drying box, the temperature probe was inserted and the box door was closed for freezing and drying according to freeze-drying curve and the final drying temperature was 35° C. or higher and maintained for 2 hours, seal the plug, exhaust the gas, take out from the box and roll the lid.

Example 39 Preparation of Rhein Conjugate Injectable Powder

| rhein conjugates | 15.0 g |
|---|---|
| mannitol | 16.0 g |
| add injectable water till | 10000 mL |

Rhein conjugates (can be conjugates of rhein arginine, lysine, glucosamine, meglumine, etc) were put into a suitable container, added with 9000 ml of injectable water and mixed evenly, then dissolved by ultrasound wave, then added with mannitol to dissolve while stirring; added with 0.1% injectable active carbon with 30 minutes of stirring, decarbonized and suctioned into a clean container through titanium sand core, supplemented injectable water to 10000 ml, mixed evenly for five minutes, and then filtered through 0.22 μm microporous membranes and the filtrate was filled into cillin bottles, and then partially plugged with rubber stopper and sent onto the lamination plate in the freeze-drying box, the temperature probe was inserted and the box door was closed for freezing and drying according to freeze-drying curve and the final drying temperature was 35° C. or higher and maintained for 2 hours, then seal the plug, exhaust the gas, take out from the box and roll the lid.

Example 39 Preparation of Rhein Conjugate or Rhein-containing Effective Part Suspension Injection

| rhein or rhein-containing effective part | 10 g |
|---|---|
| sodium carboxymethyl cellulose | 5 g |
| polysorbate 80 | 0.1 g |
| potassium dihydrogen phosphate | 8.3 g |
| potassium acid phosphate | 0.8 g |
| add injectable water till | 10.0 L |

Rhein or rhein-containing effective part was crushed by gas flow and micro powder of less than 10 μm grain diameter was obtained. Potassium dihydrogen phosphate and potassium acid phosphate were dissolved in injectable water, added with sodium carboxymethyl cellulose, completely dissolved at 60° C. and filtrated. Rhein or total rhein after micronization was put into a container, added with polysorbate 80 to grind into fine paste. The above solution was added gradually and mixed evenly and grinded for 5 times to 10 times by colloid mill. When the resulting mixture was measured and qualified according to routine method, separately placed into ampoules and then sterilized by flowing steam for 30 minutes at 100° C.

In this example, the adjuvants for the injection may be selected from the following: solubilizers such as: tweens, pluronic F-68, polyoxyethylated castor oil, etc; cosolvents such as: amino acid compounds such as histidine, lysine, carnitine; ornithine lactam compounds such as urea, acetamide, thiourea, benzamide, etc; hydroxyl or carboxyl containing compounds such as sucrose, citric acid, sodium citrate, lactic acid, sodium salicylate, etc; suspension agents such as: sodium carboxymethyl cellulose, polyvidonel, hydroxypropyl methyl cellulose, etc; pH regulators such as: citric acid and sodium citrate, phosphate, etc solvents such as: injectable water, ethanol for injection, propylene glycol, etc.

Example 41 Preparation of Rhein Arginine Conjugate Oral Solution

Rhein arginine conjugates were fully dissolved in purified water through stirring, added with 85% monosaccharide-syrup, adjusted to pH 3.5 to 7.0, then added with 0.3% sodium benzoate preservative, heated to boiling for 30 minutes, then filtered through 0.8 μm microporous membranes, filled and sealed into a 20 ml of oral brown glass bottle and then sterilized for 30 minutes at 100° C. Then, Rhein arginine conjugate oral solution was obtained.

Example 42 Preparation of Rhein Arginine Conjugate Injection

Rhein arginine conjugates were fully dissolved in injectable water, added with 0.1% active carbon, heated to boiling for 15 minutes, filtrated and suctioned carbon and adjusted to pH 5.0 to 7.0, then intermediate content and pH valued were measured; the mixture was sealed in glass ampoules after qualified, and then sterilized by flowing steam for 30 minutes at 100° C. The rhein arginine conjugates injection was obtained.

Example 43 Preparation of Rhein, Rhein Arginine Conjugate (98.0-99.9%: 0.1-2.0%) Emulsion Injection Rheins were poured into an agitation can and heated to 80° C., and then added with soybean phospholipid and mixed evenly by shearing.

Injectable water was added to a high-pressure recycling can of homogenization machine, then added with glycerol, heated to 75° C. and mixed. Homogenization machine was started, rhein, rhein and arginine and bean phospholipid mixture which have sheared and mixed evenly were added from refueling hole slowly. After finishing, close off the refueling hole, regulate high-pressure homogenization pressure to allow 10 MPa of low pressure and 32 MPa of high pressure with continuous cycle of five times, add a small amount of L-arginine or lysine with one continuous cycle of sampling test and obtain the emulsion injection by filling and sealing.

Example 44 Preparation of Rhein Arginine Conjugate Tablets

| rhein arginine conjugates | 6 g |
| microcrystalline cellulose | 40 g |
| lactose | 50 g |
| sodium carboxymethyl starch | 6 g |
| 10% starch slurry | proper amount |
| magnesium stearate | 1 g |

Rhein arginine conjugates were passed through 160 mesh sieve, and microcrystalline cellulose, lactose and sodium carboxymethyl starch are respectively passed through 100 mesh sieve; the conjugate and above dressing were evenly compounded to make soft materials with 10% starch slurry microadhesive and then passed through 20 mesh sieve to made granules. The wet granules were dried by air blasting of drying oven at 60 degree and the dry granules were passed through 20 mesh sieve to mix with magnesium stearate evenly for pressing tablets, tablet coating or enteric-coating.

Example 44 Preparation of Rhein Lysine Conjugate Capsules

| rhein lysine conjugate | 5.8 g |
| microcrystalline cellulose | 40 g |
| lactose | 50 g |
| sodium carboxymethyl starch | 6 g |
| 10% starch slurry | proper amount |
| magnesium stearate | 1 g |
| micro silicagel powder | 1 g |

Rhein and arginine conjugates were passed through 160 mesh sieve, and microcrystalline cellulose, lactose and sodium carboxymethyl starch are respectively passed through 100 mesh sieve; the conjugates and above dressing were evenly compounded to make soft materials with 10% starch slurry micro-adhesive and then passed through 20 mesh sieve to made granules. The wet granules were dried by air blasting of drying oven at 50 degree and the dry granules were passed through 20 mesh sieve to mix with magnesium stearate and micro silicagel powder evenly and filled into capsules.

Example 46 Preparation of Rhein Lysine Conjugate Oral Solution

Rhein lysine conjugates were fully dissolved in purified water through stirring, added with 85% monosaccharide syrup, adjusted to pH 5.5 to 8.5, then added with 0.3% sodium benzoate preservative, heated to boiling for 30 minutes, then filtered through 0.8 μm microporous membranes, filled and sealed into a 20 ml of oral brown glass bottle and then sterilized for 30 minutes at 100° C. Then, rhein lysine conjugate oral liquid solution was obtained.

Example 47 Preparation of Rhein Glucosamine Conjugate Injection for Bone Articular Cavity Rhein lysine conjugates were fully dissolved in injectable water, added with 0.1% active carbon, heated to be boiling for 15 minutes, filtrated and suctioned carbon and adjusted to pH 5.5 to 8.5, then intermediate content and pH valued were measured; filled and sealed in glass ampoules after qualified, and then sterilized by flowing steam for 30 minutes at 100° C. The rhein lysine conjugate injection was obtained.

Example 48 Preparation of Rhein Glucosamine Conjugate Injection for Bone Articular Cavity Rhein glucosamine conjugates were fully dissolved in injectable water, added with 0.1% active carbon, heated to boiling for 15 minutes, filtrated and suctioned carbon and adjusted to pH 5.5 to 8.5, then intermediate content and pH valued were measured; filled and sealed in glass ampoules after qualified, and then sterilized by flowing steam for 30 minutes at 100° C. The rhein lysine conjugate injection for bone articular cavity was obtained.

Example 49 Comparison of Different Rhein or Rhein-containing Effective Part Metal Salts or Conjugates Hydro-acupuncture Injection Proper amount of different rhein or rhein-containing effective part metal salts or conjugates were put into a 10 ml volumetric flask, added with water, shaken and dissolved for constant volume, and then a water-carrier preparation was obtained. Rhein or rhein-containing effective part sodium salts or sylvan preparation are adjusted to the original pH with diluted hydrochloric acid and the results were shown in Table 4.

TABLE 4

| compound | concentration | PH value | clarity | Note |
| --- | --- | --- | --- | --- |
| Rhein sodium salt | 2.0 mg/ml | 9-10 | clear | pH value of the preparation is slightly higher, unacceptable in pharmacy |
| Rhein sodium salt | 2.0 mg/ml | 6-7 | Unclear | Preparation is unclear, unacceptable in pharmacy |
| Rhein sylvin | 2.0 mg/ml | 9-10 | clear | pH value of the preparation is slightly higher, unacceptable in pharmacy |
| Rhein sodium salt | 2.0 mg/ml | 6-7 | Unclear | Preparation is unclear, unacceptable in pharmacy |
| rhein arginine conjugate | 2.0 mg/ml | 6-7 | clear | pH value and clarity accord with the requirement in pharmacy |
| rhein arginine conjugate | 2.0 mg/ml | 6-7 | clear | pH value and clarity accord with the requirement in pharmacy |
| rhein glucosamine conjugate | 2.0 mg/ml | 6-7 | clear | pH value and clarity accord with the requirement in pharmacy |
| rhein meglumine conjugate | 2.0 mg/ml | 6-7 | clear | pH value and clarity accord with the requirement in pharmacy |
| rhein carnitine conjugate | 2.0 mg/ml | 6-7 | clear | pH value and clarity accord with the requirement in pharmacy |
| rhein ligustrazine conjugate | 2.0 mg/ml | 6-7 | clear | pH value and clarity accord with the requirement in pharmacy |
| sodium salt of 50% rhein-containing effective part | 2.0 mg/ml | 9-11 | clear | pH value of the preparation is slightly higher, unacceptable in pharmacy |
| sodium salt of 50% rhein-containing effective part | 2.0 mg/ml | 6-7 | Unclear | Preparation is unclear, unacceptable in pharmacy |
| sodium salt of 50% rhein-containing effective part | 2.0 mg/ml | 9-11 | clear | pH value of the preparation is slightly higher, unacceptable in pharmacy |
| sodium salt of 50% rhein-containing effective part | 2.0 mg/ml | 6-7 | Unclear | Preparation is unclear, unacceptable in pharmacy |
| arginine conjugate of 50% rhein-containing effective part | 2.0 mg/ml | 6-7 | clear | pH value and clarity accord with the requirement in pharmacy |
| lysine conjugate of 50% rhein-containing effective part | 2.0 mg/ml | 6-7 | clear | pH value and clarity accord with the requirement in pharmacy |
| glucosamine conjugate of 50% rhein-containing effective part | 2.0 mg/ml | 6-7 | clear | pH value and clarity accord with the requirement in pharmacy |
| meglumine conjugate of 50% rhein-containing effective part | 2.0 mg/ml | 6-7 | clear | pH value and clarity accord with the requirement in pharmacy |

Example 50 Comparison of Safety of Rhein Sodium Salt or Rhein Arginine Conjugate Hydro-acupuncture Injection In rabbits' ear marginal vein aseptic operation, rhein sodium salt, rhein arginine conjugates and 0.9% sodium chloride injection liquid were slowly filled into the veins respectively every two days for three consecutive times. The results showed that, compared with the control group, rhein arginine conjugate has no irritation on rabbits' ear marginal veins, and the blood structure of the rabbits' ear marginal vein through biopsy was normal without endothelial injuries, thrombosis and other pharmacological change; rhein sodium salt has irritation on rabbits' ear marginal veins and the vasodilatation of the rabbits' ear marginal vein through biopsy was slight with partial endothelial cell necrosis and abscission, and inflammatory response of the surrounding tissues.

Example 51 Curative Effect of Rhein Lysine Conjugate on Type 2 Diabetic Nephrosis, Hyperlipidemia and Insulin Resistance in Rats Test 1 Effect of rhein lysine conjugate on diabetic nephrosis of obese diabetic in rats Drug: Rhein lysine conjugate Animal model of diabetic rats: after one month of high-fat high-sugar diet, the rats (about 180 g) were injected by subpathogenic dose (25 mg/kg) of streptozotocin (STZ) to induce the occurrence of diabetes. The model has the characteristics of moderate hyperglycemia, hyperlipidemia and insulin resistance as well as pathological changes of typical diabetic nephrosis.

Test grouping:
1. Conventional feedstuff control group: distilled water.
2. Diabetes model group: distilled water.
3. Rhein lysine diabetes treatment group: a month after STZ injection, rhein lysine complex [prepared with distilled water, intragastric infusion for rats according to 90 mg/kg (0.209 mmol/kg) dose] was administered referred to treatment group 1.
4. Rhein sodium diabetes treatment group: a month after STZ injection, rhein sodium [prepared with distilled water, intragastric infusion for rats, according to 65 mg/kg (0.212 mmol/kg) dose] was administered, referred to treatment group 2.
5. Rhein lysine diabetes prevention group: one week after STZ injection, rhein lysine conjugates were administered [prepared with distilled water and intragastric infusion for rats, according to 90 mg/kg (0.209 mmol/kg) dose], referred to prevention group 1.
6. Rhein sodium diabetes prevention group: one week after STZ injection, rhein sodium were administered [prepared with distilled water and intragastric infusion for rats, according to 65 mg/kg (0.212 mmol/kg ) dose], referred to prevention group 2.

The results are shown in Table 5 and Table 6.

TABLE 5

Effect of Rhein lysine conjugate on the biochemical and morphological index of diabetes in rats after six months of preventive administration ($\overline{X} \pm SD$, n = 10)

| Item | Control group | Model group | Prevention group 1 | Prevention group 2 |
|---|---|---|---|---|
| Urine protein (mg/24 h) | 3.12 ± 1.13 | 22.48 ± 5.16** | 10.23 ± 3.34# | 11.54 ± 2.98# |
| Weight (g) | 242 ± 11 | 228 ± 17* | 248 ± 13# | 243 ± 12# |
| Kidney weight index (double kidney weight/body weight × 10$^4$) | 5.23 ± 0.42 | 7.03 ± 0.38** | 5.26 ± 0.74# | 5.21 ± 0.68# |
| blood sugar (mmol/L) | 8.0 ± 3.4 | 18.3 ± 4.6** | 14.98 ± 5.9## | 15.08 ± 5.7## |
| Serum triacylglycerol | 0.70 ± 0.39 | 3.13 ± 0.75** | 1.56 ± 0.32## | 1.68 ± 0.45## |
| Serum total cholesterol (umol/L) | 2.26 ± 0.11 | 5.46 ± 1.23** | 2.78 ± 0.21## | 2.89 ± 0.31## |
| Steady blood sugar level (mmol/L) | 6.3 ± 0.6 | 8.4 ± 0.5** | 6.2 ± 0.4## | 6.7 ± 0.8## |
| Steady insulin level (uU/ml) | 72.9 ± 3.1 | 72.7 ± 3.3 | 71.6 ± 3.5 | 72.6 ± 3.6 |

*P < 0.05 and **P < 0.01, compared with the control group;
P < 0.05 and ##P < 0.01, compared with the model group.

TABLE 6

Effect of Rhein lysine conjugate on the biochemical and morphological index of diabetes in rats after six months of treatment ($\overline{X} \pm SD$, n = 10)

| Item | Control group | Model group | Prevention group 1 | Prevention group 2 |
|---|---|---|---|---|
| Urine protein (mg/24 h) | 3.23 ± 0.82 | 23.12 ± 5.23** | 15.12 ± 5.68# | 16.15 ± 7.71# |
| Weight (g) | 254 ± 14 | 233 ± 17* | 228 ± 15# | 229 ± 16# |
| Kidney weight index (double kidney weight/body weight × 10$^4$) | 6.36 ± 0.434 | 8.45 ± 2.56** | 6.7 ± 0.78# | 6.9 ± 0.83# |
| blood sugar (mmol/L) | 7.9 ± 3.6 | 18.1 ± 5.7** | 17.4 ± 5.6## | 17.3 ± 3.3 |
| Serum triacylglycerol | 0.79 ± 0.31 | 2.81 ± 0.61** | 1.63 ± 0.39## | 1.66 ± 0.47## |
| Serum total cholesterol (umol/L) | 2.53 ± 0.72 | 5.53 ± 1.51** | 3.56 ± 0.71## | 3.71 ± 0.63## |
| Steady blood sugar level (mmol/L) | 6.3 ± 0.6 | 8.6 ± 0.8** | 5.6 ± 0.9## | 5.9 ± 0.8## |
| Steady insulin level (uU/ml) | 81.0 ± 4.4 | 75.3 ± 3.6 | 80 ± 3.5 | 81 ± 4.5 |

*P < 0.05 and **P < 0.01, compared with the control group;
P < 0.05 and ##P < 0.01, compared with the model group.

1. Effect on Urine Protein Excretion

For the rats of the prevention group and the treatment group, the urine protein content is significantly lower than that of the model group six months after administration of rhein lysine conjugates, there is significant difference between them, as shown in Table 1, 2.

2. Effect on Kidney Weight Index

For the rats of the prevention group and the treatment group, the kidney weight and kidney weight index are significantly lower than those of the model group six months after administration of rhein lysine conjugates, there is significant difference between them, as shown in Table 1, 2.

3. Effect on Blood Sugar

For the rats of the prevention group, the blood sugar level is significantly lower than that of the model group six months after administration of rhein lysine conjugates, there is significant difference between them; while in the treatment group, comparing to that of the model group, there is no significant difference of blood sugar level of them, as shown in Table 5, 6.

4. Effect on Blood Lipid

For the rats of the prevention group and the treatment group, serum cholesterol and triglyceride of them are significantly lower than those of the model group six months after administration of rhein lysine conjugates, there is significant difference between them, as shown in Table 1, 2.

5. Effect on Steady Blood Glucose and Steady Insulin Level

SSPG levels of diabetic rats were significantly higher than that of the control group rats of conventional feeding, which showed that diabetic rats were accompanied by obvious insulin resistance. Six months later, the SSPG level of the rats of the prevention group significantly reduced; similarly, the SSPG levels of the rats of the treatment group also significantly be lower than that of the rats of the model group, as shown in Table 1, 2.

Example 52 Effect of Rhein Lysine Conjugate on the Body Weight of Obese Animals

1. Obese Hyperglycemia Mice (1) Animal grouping and test method:

9-week-old obese mice of hyperglycemia were randomly divided into: rhein sodium group, non-treatment group, rosiglitazone group, rhein lysine high-dose group and low-dose group, each group has 6 mice. Kunming mice of the same age were used as the control group, which were fed by conventional feedstuff with free food and water feeding. Rhein lysine conjugates [the dose is 180 mg/kg (0.418 mmol/kg) and 90 mg/kg (0.209 mmol/kg) for intragastric infusion, prepared with distilled water], dose of the rhein sodium group is 130 mg/kg (0.424 mmol/kg), the mixture was dissolved with distilled water, intragastric administration; rosiglitazone group (the dose is 4 mg/kg), the mixture was dissolved with distilled water, intragastric administration, and the rats of the other two groups were administered with the same volume of distilled water, once a day, 12 weeks of administration in succession. The animals' body weight and blood sugar were measured regularly, and statistical analysis was conducted. The results were shown in Table 7 and 8.

TABLE 7

Body-weight changes of obese diabetes mice after rhein lysine conjugate administration ($\bar{X} \pm SD$, n = 6)

| | Prior to administration (g) | 6 w after administration (g) | 9 w after administration (g) | 12 w after administration (g) |
|---|---|---|---|---|
| Normal mice | 18.9 ± 1.3 | 23.6 ± 1.1 | 25.9 ± 0.3 | 27.5 ± 0.4 |
| Obese hyperglycemia mice | 29.1 ± 2.0** | 41.1 ± 2.3** | 46.2 ± 2.3** | 48.2 ± 1.6** |
| Rhein lysine (high) | 29.2 ± 1.6 | 34.9 ± 1.6# | 38.2 ± 1.3## | 40.1 ± 1.4## |
| Rhein lysine (low) | 28.8 ± 1.6 | 35.7 ± 1.7# | 39.3 ± 1.2## | 41.3 ± 1.6## |
| Sodium rhein | 28.9 ± 1.8 | 35.8 ± 1.5# | 39.5 ± 1.4## | 41.1 ± 1.5## |
| Rosiglitazone | 29.3 ± 1.7 | 42.1 ± 1.9 | 48.2 ± 1.5 | 50.1 ± 1.8 |

TABLE 8

Blood glucose changes of obese diabetes mice after rhein lysine conjugate administration(mmol/L) ($\bar{X} \pm SD$, n = 6)

| | Prior to administration | 6 w after administration | 9 w after administration | 12 w after administration |
|---|---|---|---|---|
| Normal mice | 10.9 ± 2.3 | 10.6 ± 2.1 | 9.9 ± 3.2 | 10.5 ± 2.4 |
| Obese hyperglycemia mice | 29.1 ± 4.0** | 34.1 ± 4.6** | 37.2 ± 6.3** | 40.2 ± 4.8** |
| Rhein lysine (high) | 29.2 ± 3.6 | 30.9 ± 4.2# | 30.2 ± 5.3## | 28.1 ± 5.4## |
| Rhein lysine (low) | 28.7 ± 5.3 | 31.4 ± 4.9# | 33.7 ± 5.6## | 30.4 ± 4.2## |
| Sodium rhein | 28.9 ± 4.8 | 31.2 ± 5.5# | 33.5 ± 5.4## | 30.1 ± 4.5## |
| Rosiglitazone | 29.3 ± 4.7 | 31.1 ± 4.9 | 30.5 ± 4.5## | 27.9 ± 3.8## |

*$P < 0.05$ and **$P < 0.01$, compared with the normal mice group;
$P < 0.05$ and ##$P < 0.01$, compared with the non-treatment group.

(2) The results showed that, the weight and blood sugar of the obese hyperglycemia mice have significant difference comparing to that of the non-treatment group 6 weeks after administration of rhein lysine conjugates; and have extremely significant difference 9 weeks after administration of rhein lysine conjugates, which indicated that the conjugates have the effects of reducing blood sugar and body weight of mice.

2. Obese Rats of High-fat and High-sugar Diet (1) Animal and animal grouping

Group A: conventional diet, 4 weeks later, started to carry on intragastric administration, and the same volume of distilled water as the control, once daily, three weeks in succession.

Group B: high-fat high-sugar diet, 4 weeks later, started to carry on intragastric administration, and the same volume of distilled water as the model control, once daily, three weeks in succession.

Group C: high-fat high-sugar diet, 4 weeks later, started to carry on intragastric administration of rhein lysine conjugates [dose: 90 mg/kg (0.209 mmol/kg), prepared by distilled water], once daily, three weeks in succession.

Group D: high-fat high-sugar diet, 4 weeks later, started to carry on intragastric administration of rhein lysine conjugates [dose: 45 mg/kg (0.105 mmol/kg), prepared by distilled water], once daily, three weeks in succession.

Group E: high-fat high-sugar diet, 4 weeks later, started to carry on intragastric administration of rhein sodium [dose: 65 mg/kg (0.212 mmol/kg), prepared by distilled water], once daily, three weeks in succession.

(2) Results

Four weeks after high-sugar high-fat diet, the body weights of the rats in the B, C, D, E groups are significantly higher than that of group A, which indicates that after high-sugar high-fat diet, obesity of rats is induced. Three weeks after the administration, the body weights of rats in the C, D and E groups are significantly lower than that of group B (Shown in Table 9).

TABLE 9

Changes of body weights of rats after administration of rhein lysine conjugate ($\overline{X} \pm SD$, n = 10)

|  | The body weight increased 4 weeks after high-sugar high-fat diet (g) | The body weight increased 7 weeks after high-sugar high-fat diet (g) |
| --- | --- | --- |
| Group A | 10.9 ± 4.8 | 19.3 ± 4.2 |
| Group B | 14.7 ± 4.2* | 31.2 ± 3.4** |
| Group C | 15.3 ± 3.8* | 16.8 ± 4.8## |
| Group D | 16.1 ± 4.2* | 17.7 ± 4.6## |
| Group E | 15.8 ± 4.3* | 17.1 ± 4.1## |

*$P < 0.05$ and **$P < 0.01$, compared with normal mice group;
$P < 0.01$ compared with the model group.

Example 53 Preparation of 1,3-dihydroxy-6-carboxyanthraquinone Arginine Conjugate The procedure was carried out basically as Example 6, but, wherein rhein should be replaced by 1,3-dihydroxy-6-carboxyanthraquinone. The conjugate was used as the drugs for treatment of diabetic nephrosis.

Example 54 Preparation of 1,3-dihydroxy-6-carboxyanthraquinone Lysine Conjugate

The procedure was carried out basically as Example 7, but, wherein rhein should be replaced by 1,3-dihydroxy-6-carboxyanthraquinone. The conjugate was used as the drugs for treatment of diabetic nephrosis; or used as the drugs of treatment of osteoarthritis, rheumatic arthritis and rheumatoid arthritis.

Example 55 Preparation of 1,3-dihydroxy-6-carboxyanthraquinone Meglumine Conjugate The procedure was carried out basically as Example 8, but, wherein rhein should be replaced by 1,3-dihydroxy-6-carboxyanthraquinone. The conjugate was used as the drugs for treatment of diabetic nephrosis.

Example 56 Preparation of 1,3-dihydroxy-6-carboxyanthraquinone Carnitine Conjugate The procedure was carried out basically as Example 10, but, wherein rhein should be replaced by 1,3-dihydroxy-6-carboxyanthraquinone. The conjugate was used as the drugs for treatment of diabetic nephrosis.

Example 58 Preparation of 1,3-dihydroxy-6-carboxyanthraquinone Glucosamine Conjugate The procedure was carried out basically as Example 6, but, wherein rhein should be replaced by 1,3-dihydroxy-6-carboxyanthraquinone. The conjugate was used as the drugs for treatment of diabetic nephrosis.

The conjugates prepared in Examples 53~58 can be used as the medicines of treatment of recovery of gastrointestinal function and prevention of intestinal adhesion; or used as the medicines of treatment of osteoarthritis, rheumatic arthritis and rheumatoid arthritis.

Example 59 Efficiency Test of Rhein Arginine on the Promotion of Recovery of Gastrointestinal Function and prevention of Intestinal Adhesion Test 1 Effect of Rhein Arginine on Capillary Permeability of Mice Sixty(60)mice, male, weighing from 18 to 22 g, were randomly divided into five groups, namely, model control group, domperidone group, rhein sodium group, rhein glucosamine large dose group and low dose group. Each group has 12 mice, administration: 0.20 ml/10 g. Mice in the model control group were administrated with isovolumic physiologic saline. After administration of drug, test were conducted according to the method in the literature [Chen Qi, Herbal pharmacology research methodology 1994:356] and the absorbance values were measured and recorded, then t test was used for the intergroup comparison. The test results are as follows (Table 10):

TABLE 10

Effect of rhein arginine on capillary permeability of mice ($\overline{X} \pm SD$, n = 12)

| group | dosage (mg/kg) | absorbance value |
| --- | --- | --- |
| model control group | — | 0.606 ± 0.151 |
| hydrocortisone | 40 | 0.312 ± 0.097** |
| rhein arginine large dose group | 24 | 0.455 ± 0.105** |
| rhein arginine low dose group | 12 | 0.476 ± 0.096* |
| rhein sodium group | 12 | 0.494 ± 0.134* |

*$P < 0.05$, **$P < 0.01$ compared with the model control group.

The test results showed that, comparing to the model control group, there is obvious effect on the inhibition of capillary permeability of mice in the rhein arginine large dose group, low dose group and rhein sodium group.

Test 2 Effect of Rhein Arginine on the Formation of Granuloma in Rats

Rats were randomly divided into five groups (model control group, indomethacin group, rhein glucosamine large dose group and low dose group and rhein sodium group). Each group included 10 rats, and built models according to the method in the literature [Xu Shuyun, Methodology in Pharmacological Experiment (the 3rd version): 918]. The rats were administered by medicines from the day when starting the operation. For the rats of indomethacin group, intramuscular injection was carried on according to the dosage of 10 mg/kg, administration volume: 0.4 ml/100 g; for the rats of physiologic saline group and administration group, the administration volume for each time by intragastric administration is 0.4 ml/100 g. The rats were killed in two weeks, and tests were performed according to the methods in the literature, the net weight of granulation was calculated, and t test was used for the intergroup comparison. The test results were as follows (Table 11):

TABLE 11

Effect of rhein arginine on the formation of granuloma in rats ($\bar{X} \pm SD$, n = 10)

| group | dosage (mg/kg) | net weight of granulation (mg) |
|---|---|---|
| model control group | — | 19.20 ± 3.52 |
| indomethacin group | 10 | 12.21 ± 2.43** |
| rhein glucosamine large dose group | 24 | 13.64 ± 2.47** |
| rhein glucosamine low dose group | 12 | 15.23 ± 3.60** |
| rhein sodium group | 12 | 15.87 ± 3.31** |

* $P < 0.01$ compared with model control group.

The test results showed that, comparing to the result of the model group, there is a significant effect on the inhibition of the formation of cotton ball granuloma in rats of ig rhein arginine large dose group, low dose group, and rhein sodium group respectively, $p<0.01$.

Test 3 Effect of Rhein Arginine on the Intestinal Propulsion in Mice

Fifty mice, male, weighting from 18 to 22 g, were randomly divided into five groups, namely, model control group, domperidone group, rhein sodium group, rhein glucosamine large dose group and low dose group.

Each group has 10 mice respectively. The mice were fasted, but water was not prohibited, and then administered with medicines by intravenous injection. After that, tests were carried on immediately according to the methods in the literature[Xu Shuyun, Methodology in Pharmacological Experiment (the 3rd version): 1313]. The intestinal propulsive rates were calculated, and t test was used for the intergroup comparison. The test results were as follows (Table 12):

TABLE 12

Effect of rhein arginine on the intestinal propulsion in mice ($\bar{X} \pm SD$, n = 10)

| Group | Dosage (mg/kg) | Propulsive rate (%) |
|---|---|---|
| model control group | — | 45.63 ± 10.1 |
| domperidone control group | 9 | 55.42 ± 9.6** |
| rhein arginine large dose group | 24 | 66.47 ± 9.7** |
| rhein arginine low dose group | 12 | 53.81 ± 8.9** |
| rhein sodium group | 12 | 51.69 ± 7.1** |

**$p < 0.01$ compared with model control group.

The test results showed that: comparing to the result of the control group, there is a significant effect on the intestinal propulsion in mice of the rhein arginine large dose group, rhein arginine low dose group and rhein sodium group respectively, $p<0.01$.

Test 4 Effect of Rhein Arginine on Intestinal Adhesion in Rats

Rats were fasted for 12 h and models were built according to the methods in the literature [Xu Shuyun, Methodology in Pharmacological Experiment (the 3rd version): 1335]. The rats were randomly divided into five groups, namely, model control group, dexamethasone group, rhein sodium group, rhein glucosamine large dose group and low dose group. Each group included 12 rats. The rats were administered with medicines once a day, the administration volume of 0.4 ml/100 g. The rats of the model group were administered with the same volume of NS, while the rats of the positive control group were administered with dexamethasone, administered once every two days, dose: 10 mg/kg. The administration volume was the same as the treatment group. The rats were killed on the $7^{th}$ day and carried on laparotomy. Adhesion degree was classified and scored respectively. The classification and score of the observed index-adhesion degree can refer to the five-grade classification method prepared by Nair, and determine the classification standard, see Schedule 13. Intestinal adhesion classification adopts Ridit analysis. The test results are as follows (Table 14):

TABLE 13

Rating Evaluation Standard of Intestinal Adhesion Degree

| Rate | Status of adhesion |
|---|---|
| 0 | completely no adhesion |
| I | One adhering zone between internal organs or between internal organ and abdominal wall |
| II | Two adhering zones between internal organs or between internal organ and abdominal wall |
| III | More than two adhering zones and the internal organs do not adhere to the abdominal wall directly |
| IV | the internal organs adhere to the abdominal wall directly, no matter how many adhering zones |

TABLE 14

Effect of rhein arginine on intestinal adhesion in rats

| group | dosage (mg/kg) | Rating of adhesion degree | | | | |
|---|---|---|---|---|---|---|
| | | 0 | I | II | III | IV |
| model control group | | 0 | 0 | 2 | 7 | 3 |
| dexamethasone group | 10 | 1 | 2 | 8 | 1 | 0 |
| rhein arginine large dose group | 12 | 3 | 5 | 2 | 2 | 0 |
| rhein arginine low dosage group | 6 | 1 | 4 | 3 | 3 | 1 |
| rhein sodium group | 6 | 1 | 4 | 2 | 3 | 2 |

The results showed that the abdominal adhesion ratings of the rhein arginine large dose group and low dose group and rhein sodium group have statistical significances comparing to that of the control group($p<0.05$).

Example 59 Effect of Rhein Glucosamine Conjugates on the Treatment of Arthritis

1. Effect of Xylene on the Swelling of Auricle in Mice

Fifty male Kunming mice were selected, weighing 18-22 g each, and randomly divided into five groups, namely, model control group, aspirin group, rhein sodium group, rhein glucosamine large dose group and low dose groups. Each group had 10 mice respectively. The mice were administered with medicines by intragastric administration every day, for 0.2 ml/10 g body weight. The mice of the model control group were administered with equal volume of physiological saline, once every day, continuously administration for 3 days. After 60 minutes of the final administration, carried on test according to the method in the literature [Xu Shuyun, Methodology in Pharmacological Experiment (the 3rd version): 911]. The sweeling degree of auricle was calculated and statistical analysis was conducted. The test results are shown in Table 15.

TABLE 15

Effect of rhein glucosamine on the xylene-induced swelling of auricle in mice
($\overline{X} \pm SD$, n = 10)

| Group | Dosage(mg/kg) | swelling degree of auricle (g) | inhibition rate (%) |
|---|---|---|---|
| model control | — | 17.8 ± 2.4 | — |
| aspirin | 200 | 9.1 ± 1.8** | 48.9 |
| rhein glucosamine | 80 | 10.3 ± 2.6** | 42.1 |
|  | 40 | 12.3 ± 2.1** | 30.9 |
| rhein sodium | 40 | 12.5 ± 2.2** | 29.8 |

**$P < 0.01$ compared with model control group

The results showed that, rhein glucosamine has obvious inhibitory effect on the xylene-induced swelling of auricle in mice, comparing to the model control group, there is extremely significant difference ($P<0.01$).

2. Effect on the Acute Pleurisy Exudation and Leukoplania in Rats

Forty male rats of 200±20 g weight were selected and divided into five groups, namely, model control group, indomethacin group, rhein sodium group, rhein glucosamine large dose group and small dose group. Eight rats for each group. The rats were administered with medicines by intraperitoneal administration, one hour later, the rats were induced with acute pleurisy by carrageenan according to the method in the literature [Xu Shuyun, Methodology in Pharmacological Experiment (the 3rd version): 916]. Four hours later, the rats were killed and the volume of pleural effusion and total white cell count were measured. The results are shown in Table 16.

TABLE 16

Effect of rhein glucosamine on acute pleurisy exudation and leukoplania in rats
($\overline{X} \pm SD$, n = 8)

| Group | Dosage (mg/kg) | Volume of exudation fluid | WBC (×109/L) |
|---|---|---|---|
| model control | — | 0.79 ± 0.24 | 8.98 ± 1.46 |
| indomethacin group | 10 | 0.26 ± 0.11** | 3.01 ± 1.59** |
| rhein glucosamine | 40 | 0.28 ± 0.13** | 3.10 ± 1.09** |
|  | 20 | 0.31 ± 0.18* | 3.87 ± 1.76* |
| rhein sodium | 20 | 0.33 ± 0.12* | 3.98 ± 1.64* |

*$P < 0.05$, **$P < 0.01$ compared with the model control group.

The results showed that, the rats of the rhein glucosamine large dose group and low dose group can significantly resist the carrageenan-induced acute pleurisy exudation and leukoplania in rats.

3. Effect on the Immune Function in Mice

Fifty Kunming mice, half male and half female, weighing 18-22 g each, were selected and randomly divided into five groups, namely, model control group, cyclophosphamide group, rhein sodium group, rhein glucosamine large dose group and small dose group, 10 mice for each group. The mice were administered with medicines by intragastric administration, 0.2 ml/10 g body weight, once every day and administered for 3 days in succession. After the mice were administered with medicines, 30 minutes later, test was carried on according to the method in the literature [Xu Shuyun, Methodology in Pharmacological Experiment (the 3rd version): 934]. The phagocytic index K and corrected phagocytic index α were calculated, and t-test was conducted for statistical analysis. The results are shown in Table 17.

TABLE 17

Effect of rhein glucosamine on the immune function in mice ($\overline{X} \pm SD$, n = 10)

| Group | Dosage (mg/kg) | Clearance index (k) | Phagocytic index (α) |
|---|---|---|---|
| model control | — | 0.0354 ± 0.0141 | 5.498 ± 0.6301 |
| cyclophosphamide | 20 | 0.0192 ± 0.0102** | 4.0208 ± 0.6698** |
| rhein glucosamine | 80 | 0.0221 ± 0.0086** | 4.4549 ± 0.7237** |
|  | 40 | 0.0265 ± 0.0102* | 4.8725 ± 0.7246* |
| rhein sodium | 40 | 0.0272 ± 0.0124* | 4.9134 ± 0.7498* |

**$P < 0.01$ compared with the model control group.

The results showed that, rhein glucosamine can reduce the clearance index and phagocytic index in mice, which indicated it has the function of regulating immune function.

4. Effect of Rhein Glucosamine on the Formation of Granuloma in Rats

Rats were randomly divided into five groups (model control group, indomethacin group, rhein glucosamine large dose group and small dose group and rhein sodium group). Each group has 10 mice. According to the method in the literature [Xu Shuyun, Methodology in Pharmacological Experiment (the 3rd version): 918], the models were built, and the rats were administered with medicines since the day when starting operations. Intramuscular injection of indomethacin 10 mg/kg, administration volume: 0.41 ml/100 g; for the physiological saline group and medicine administration group, the administration volume for each time: 0.4 ml/100 g, intragastric administration. Two weeks later, the rats were killed and test was carried on according to the method in the literature. The net weight of granulation was calculated, and t test was used for the intergroup comparison. The results are shown as follows (Table 18):

TABLE 18

Effect of rhein glucosamine on the formation of granuloma in rats ($\overline{X} \pm SD$, n = 10)

| Group | Dosage (mg/kg) | Net weight of granulation (mg) |
|---|---|---|
| model control group | — | 19.20 ± 3.52 |
| indometacin group | 10 | 12.17 ± 2.49** |
| rhein glucosamine large dose group | 40 | 12.94 ± 2.34** |
| rhein glucosamine low dose group | 20 | 14.73 ± 3.15** |
| rhein sodium group | 20 | 15.23 ± 2.99ΔΔ |

**$P < 0.01$, compared with the physiological saline group.

The results showed that, comparing to results of the model group, there is obviously inhibitory effect on the formation of granuloma in rats in the ig rhein glucosamine large dose group and low dose group, $p<0.01$.

5. Effect on Acetic Acid-induced Writhing Response in Mice

Fifty Kunming mice, half male and half female, weighing 18-22 g each, were selected and randomly divided into five groups, namely, model control group, aspirin group, rhein sodium group, rhein glucosamine large dose group and small dose group, 10 mice for each group. The mice were administered with medicine by intragastric administration every day, 0.2 ml/10 g body weight, once every day, and administered for 12 days in succession. After the final administration of medicines, 30 minutes later, test was carried on according to the methods in the literature [Xu Shuyun, Methodology in Pharmacological Experiment (the 1st version): 882]. The inhibiting rate for writhing response was calculated. The results are shown in Table 19.

TABLE 19

Effect of rhein glucosamine on writhing response in mice ($\overline{X} \pm SD$, n = 10)

| Group | Dosage (mg/kg) | Times of writhing (per/20 min) | Inhibiting rate (%) |
| --- | --- | --- | --- |
| Model control | — | 32.3 ± 5.4 | |
| Aspirin group | 200 | 11.1 ± 6.3** | 65.6 |
| Rhein glucosamine | 80 | 16.6 ± 8.7** | 48.6 |
|  | 40 | 20.3 ± 9.2* | 37.1 |
| Rhein sodium | 40 | 20.1 ± 8.9* | 37.7 |

*P < 0.05, **P < 0.01 compared with model control group.

Test results showed that, comparing to the model group, there is obviously inhibitory effect on the occurrence of acetic acid-induced writhing response in mice in the ig rhein glucosamine large dose group and low dose group. Comparing to the model group, there is significant difference, which indicates that rhein glucosamine has analgesic effect.

The above five tests showed that, rhein glucosamine prepared herein has the functions of anti-inflammation, immune regulation and analgesic effect, and can be used in the treatment of arthritis.

The invention claimed is:

1. A conjugate of at least one rhein of general formula (I)

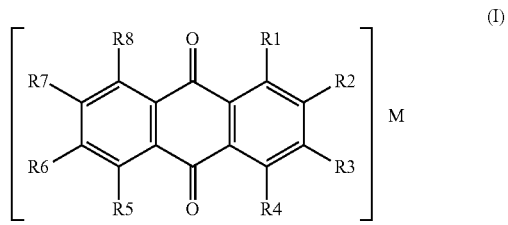

wherein two of substituents R2, R3, R6 or R7 are COOH; the remaining substituents are selected from the group consisting of H, O-glucose, OH, OCH3 and CH3; at least two, and at most six, of substituents R1-R8 are H; M is at least one member selected from nitrogen-containing organic bases or basic amino acids; and wherein the at least one rhein combines with the nitrogen-containing organic bases or basic amino acids to form the conjugate.

2. The conjugate of claim 1, wherein the content of rhein is within the range of 50 ~99%.

3. The conjugate of claim 2, wherein said rhein is extracted from at least one of the following: Rheum plamatum L, Rheum tanguticum Maxim, ex Balf or Rheum officinale Baill, Polygonum cuspidatum Sieb.et Zucc, and Folium sennae.

4. The conjugate of claim 1, wherein said nitrogen-containing organic bases and the basic amino acids are selected from the group consisting of arginine, lysine, carnitine, meglumine, glucosamine, and ligustrazine.

* * * * *

UNITED STATES PATENT AND TRADEMARK OFFICE
CERTIFICATE OF CORRECTION

| | | |
|---|---|---|
| PATENT NO. | : 9,181,172 B2 | Page 1 of 1 |
| APPLICATION NO. | : 11/995363 | |
| DATED | : November 10, 2015 | |
| INVENTOR(S) | : Xiaodong Cong | |

It is certified that error appears in the above-identified patent and that said Letters Patent is hereby corrected as shown below:

In the Specification,

Column 6, line 19, please change "formua" to --formula--

Column 10, line 28, please change "methy" to --methyl--

Column 12, line 31, please change "mergered" to --merged--

Signed and Sealed this
Twenty-first Day of June, 2016

Michelle K. Lee
*Director of the United States Patent and Trademark Office*